US012648775B2

(12) United States Patent
Liu et al.

(10) Patent No.: US 12,648,775 B2
(45) Date of Patent: Jun. 9, 2026

(54) SURGICAL INSTRUMENT CONFIGURED TO DETERMINE TREATMENT MODALITY DURING TISSUE CLAMPING

(71) Applicant: CILAG GMBH INTERNATIONAL, Zug (CH)

(72) Inventors: Zhijun Liu, Mason, OH (US); Douglas Marriott, Maineville, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 119 days.

(21) Appl. No.: 18/609,348

(22) Filed: Mar. 19, 2024

(65) Prior Publication Data

US 2025/0295409 A1 Sep. 25, 2025

(51) Int. Cl.
| | |
|---|---|
| *A61B 17/072* | (2006.01) |
| *A61B 34/37* | (2016.01) |
| *A61B 17/00* | (2006.01) |
| *A61B 17/29* | (2006.01) |
| *A61B 34/30* | (2016.01) |
| *A61B 90/00* | (2016.01) |

(52) U.S. Cl.
CPC ........ *A61B 17/07207* (2013.01); *A61B 34/37* (2016.02); *A61B 2017/00022* (2013.01); *A61B 2017/00398* (2013.01); *A61B 2017/07271* (2013.01); *A61B 2017/2927* (2013.01); *A61B 2034/301* (2016.02); *A61B 2090/061* (2016.02)

(58) Field of Classification Search
CPC . A61B 17/068; A61B 17/07207; A61B 34/37; A61B 2034/301; A61B 2017/00022; A61B 2017/00398; A61B 2017/07271; A61B 2017/2927
See application file for complete search history.

(56) References Cited

U.S. PATENT DOCUMENTS

| | | | |
|---|---|---|---|
| 7,464,847 | B2 | 12/2008 | Viola et al. |
| 8,210,413 | B2 | 7/2012 | Whitman et al. |
| 11,589,863 | B2 | 2/2023 | Weir et al. |
| 2018/0360445 | A1 | 12/2018 | Shelton, IV |
| 2021/0145441 | A1 | 5/2021 | Weir et al. |
| 2021/0361376 | A1* | 11/2021 | Eschbach ......... A61B 17/07207 |
| 2024/0041455 | A1 | 2/2024 | Shelton, IV |

OTHER PUBLICATIONS

International Search Report and Written Opinion from PCT Application No. PCT/IB2025/052802, dated Jun. 4, 2025.
Huang, et al., A Thickness Calibration Device is Needed to Determine Staple Height and Avoid Leaks in Laparoscopic Sleeve Gastrectomy, OBES SURG, Springerlink.com, May 30, 2015.

* cited by examiner

*Primary Examiner* — Michelle Lopez
(74) *Attorney, Agent, or Firm* — Troutman Pepper Locke LLP

(57) ABSTRACT

Surgical instruments, methods, and software are presented herein that are configured to actuate an end effector to grasp between the pair of jaws, compress tissue during a tissue relaxation time period in which grasped tissue relaxes between the pair of jaws, monitor a motor parameter of the motor during at least a portion of the tissue relaxation time period, extract a mathematical feature of the motor parameter during at least a portion of the tissue relaxation time period, and determine a treatment modality based at least in part on the mathematical feature.

20 Claims, 15 Drawing Sheets

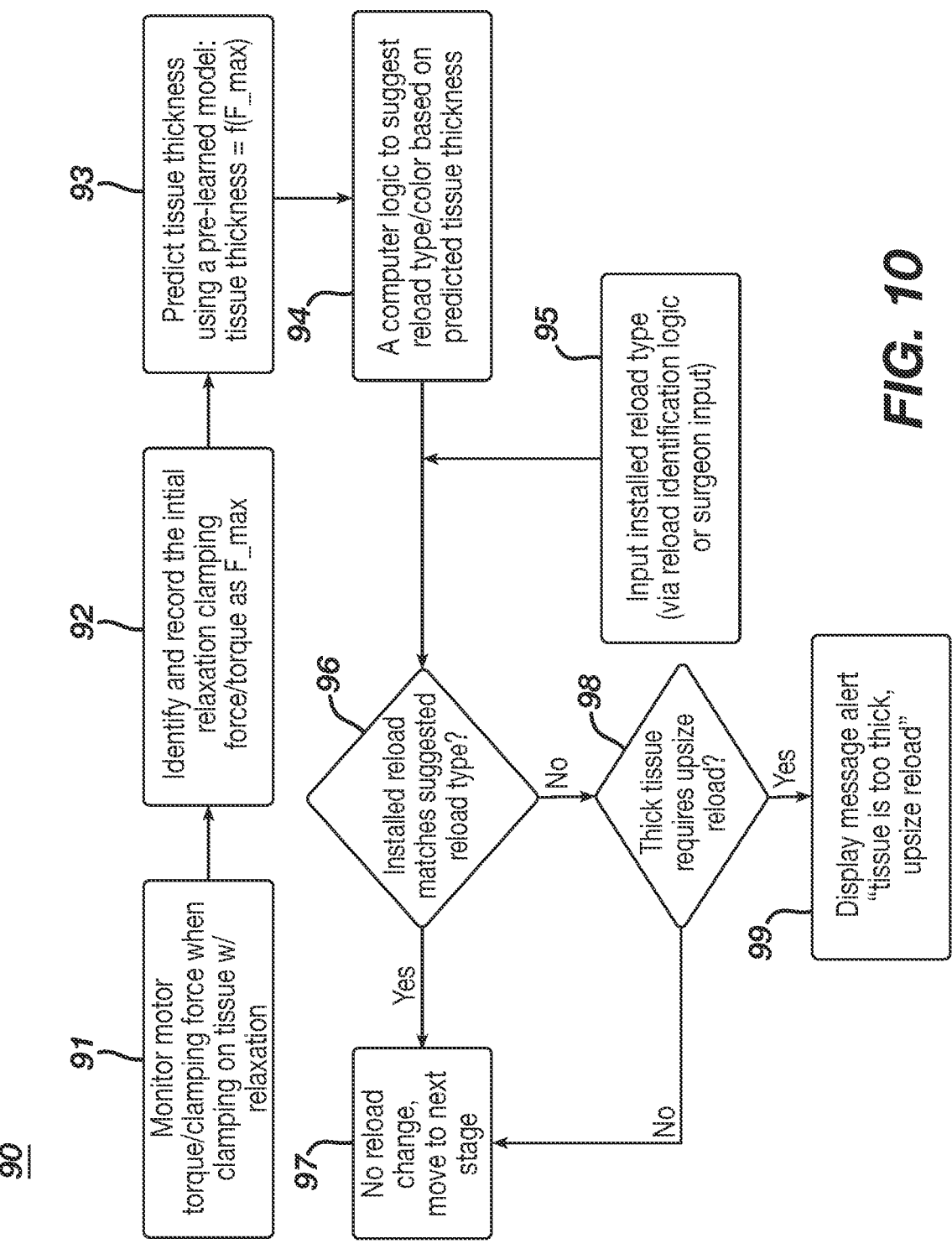

90

91 — Monitor motor torque/clamping force when clamping on tissue w/ relaxation

92 — Identify and record the intial relaxation clamping force/torque as F_max

93 — Predict tissue thickness using a pre-learned model: tissue thickness = f(F_max)

94 — A computer logic to suggest reload type/color based on predicted tissue thickness 95 — Input installed reload type (via reload identification logic or surgeon input)

96 — Installed reload matches suggested reload type?

97 — No reload change, move to next stage

98 — Thick tissue requires upsize reload?

99 — Display message alert "tissue is too thick, upsize reload"

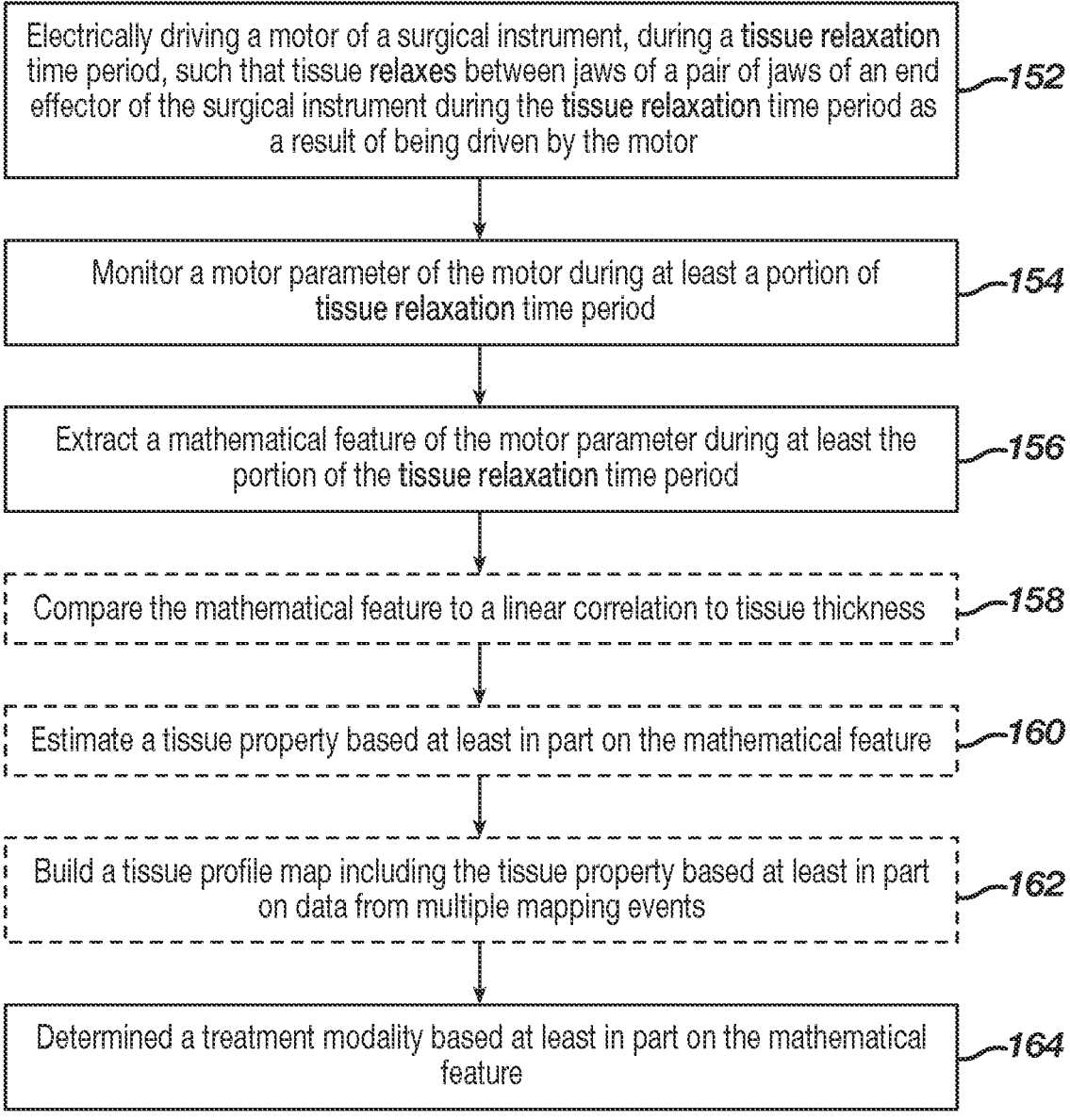

Electrically driving a motor of a surgical instrument, during a tissue relaxation time period, such that tissue relaxes between jaws of a pair of jaws of an end effector of the surgical instrument during the tissue relaxation time period as a result of being driven by the motor —152

Monitor a motor parameter of the motor during at least a portion of tissue relaxation time period —154

Extract a mathematical feature of the motor parameter during at least the portion of the tissue relaxation time period —156

Compare the mathematical feature to a linear correlation to tissue thickness —158

Estimate a tissue property based at least in part on the mathematical feature —160

Build a tissue profile map including the tissue property based at least in part on data from multiple mapping events —162

Determined a treatment modality based at least in part on the mathematical feature —164

FIG. 12A

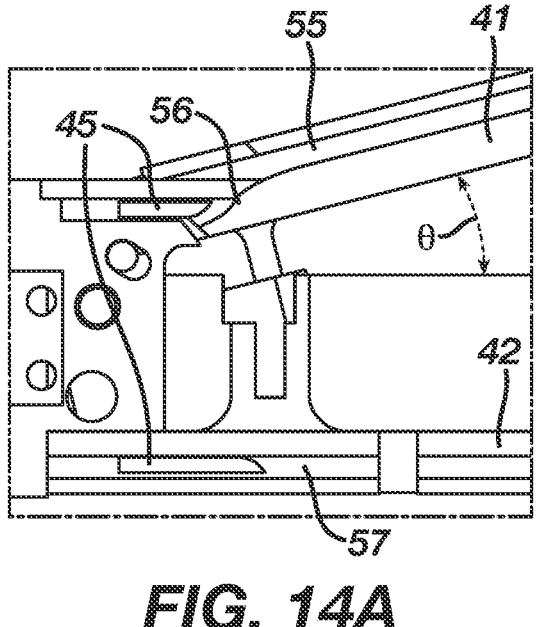
FIG. 14A
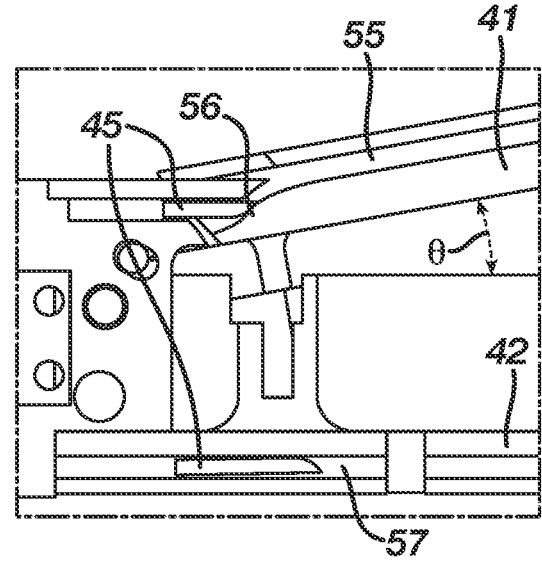
FIG. 14B
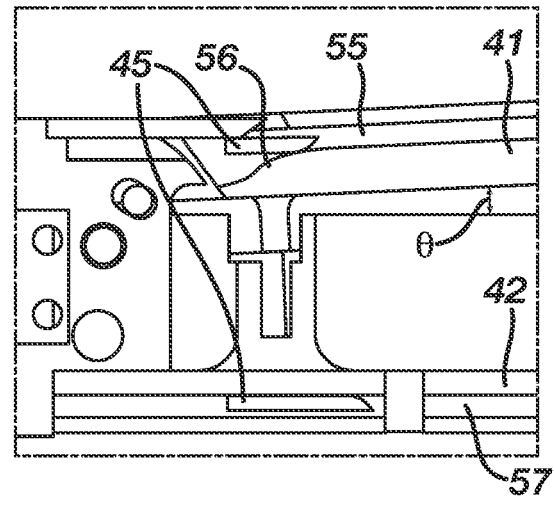
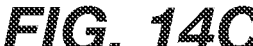
FIG. 14C
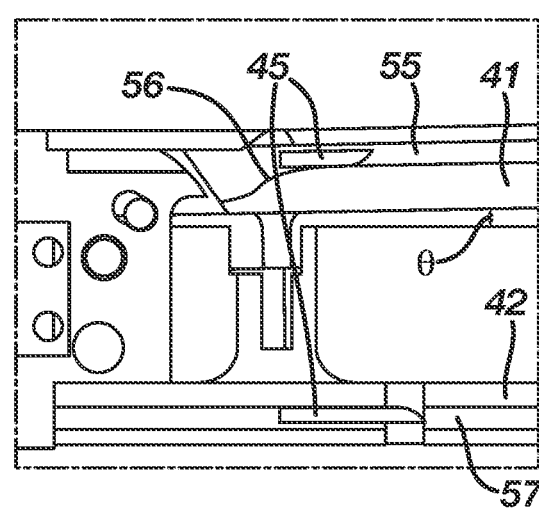
FIG. 14D

SURGICAL INSTRUMENT CONFIGURED TO DETERMINE TREATMENT MODALITY DURING TISSUE CLAMPING

FIELD

This application relates generally to medical devices, and in particular to motor driven surgical staplers.

BACKGROUND

Tissue compression is a consideration in surgical operations such as surgical stapling, suturing, cauterization, temporary clamping, and other operations involving cutting and/or sealing tissue. Surgical instruments configured to cut and/or seal tissue can have treatment modalities that are dependent on properties of tissue that is being treated. For instance, a surgical stapler can utilize a staple accessory such as a staple cartridge or an end effector, which is indicated for use with tissue having a given thickness. In many current treatments involving surgical staplers, a physician estimates tissue thickness and selects a stapler accessory indicated for use with a corresponding tissue thickness. Likewise, aspects of a treatment involving other types of surgical instruments configured to cut and/or seal tissue (e.g., energy-based surgical instruments) may be tailored based on certain tissue properties. During such treatments, tissue is clamped between a pair of jaws, which can be done mechanically through manual manipulation of levers to apply force to the jaws or electrically powered by driving a motor to apply force to the jaws. Powered surgical instruments can be handheld or robotic.

There exists a need for improved or alternative surgical instruments, methods, and systems for determining and/or delivering a treatment modality appropriate for tissue being treated.

SUMMARY

Examples disclosed herein generally describe powered surgical instruments and associated software to assist in selecting a treatment modality appropriate for tissue being treated based on a motor parameter of a motor driving closure and/or clamping of jaws of an end effector of the surgical instrument. In some aspects, instruments and methods disclosed herein can be used for tissue thickness prediction and/or estimation based on a motor parameter such as torque, force, or speed, during tissue relaxation of end effector in clamping or grasping stages. A mathematical feature of the motor parameter during tissue relaxation can be input into a pre-learned correlation model to estimate or predict tissue thickness. In some examples, the mathematical feature includes a maximum motor torque (or closure force) at a start of a tissue relaxation time period which occurs immediately after the end of an end effector closure time period. For instance, jaws can be closed around tissue during the end effector closure time period, and once the jaws are closed and in contact with tissue, tissue relaxes between the closed jaws during the tissue relaxation time period. The surgical instrument can be configured such that a mathematical correlation (e.g., linear correlation) exists between the mathematical feature and the predicted/estimated tissue thickness. The predicted/estimated tissue thickness can then be used to inform treatment modality. In the case of a surgical stapler, the mathematical feature of the motor parameter during the end effector relaxation stage (which is correlated to tissue thickness) can be used to provide an indication of appropriate staple selection (e.g., selection of an end effector or cartridge reload indicated for a predetermined tissue thickness or range of thicknesses). In some examples, multiple mathematical features of the motor parameter during a relaxation stage can be used to predict/estimate tissue thickness and/or provide an indication of a treatment modality appropriate for the treated tissue.

In one example, a surgical instrument includes an end effector, a motor assembly, and a motor control circuit. The end effector includes a pair of jaws. The motor assembly includes a motor mechanically coupled to the end effector. The motor assembly is configured to actuate the end effector to grasp and compress tissue between the pair of jaws. The motor control circuit is configured to electrically drive the motor during a relaxation time period, monitor a motor parameter of the motor during at least a portion of the relaxation time period, extract a mathematical feature of the motor parameter during at least a portion of the relaxation time period, and determine a treatment modality based at least in part on the mathematical feature.

In another example, a method can include the following steps performed in a variety of orders and with intervening steps as understood by a person skilled in the art. The method can include electrically driving a motor of a surgical instrument during a relaxation time period, such that tissue is clamped between jaws of a pair of jaws of an end effector of the surgical instrument during the relaxation time period as a result of being driven by the motor. The method can include monitoring a motor parameter of the motor during at least a portion of the relaxation time period. The method can include extracting a mathematical feature of the motor parameter during at least the portion of the relaxation time period. The method can include determining a treatment modality based at least in part on the mathematical feature.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements. The figures depict one or more implementations of the inventive devices, by way of example only, not by way of limitation.

FIG. 10 is a flow diagram illustrating a method for determining a treatment modality during a relaxation time period and providing user feedback.

FIGS. 12A is a flow diagram illustrating another method for determining a treatment modality during a relaxation time period.

FIGS. 14A, 14B, 14C, and 14D are a sequence of illustrations of a clamping assembly of an end effector during a closing time period and a relaxation time period.

DETAILED DESCRIPTION

Figure 1:
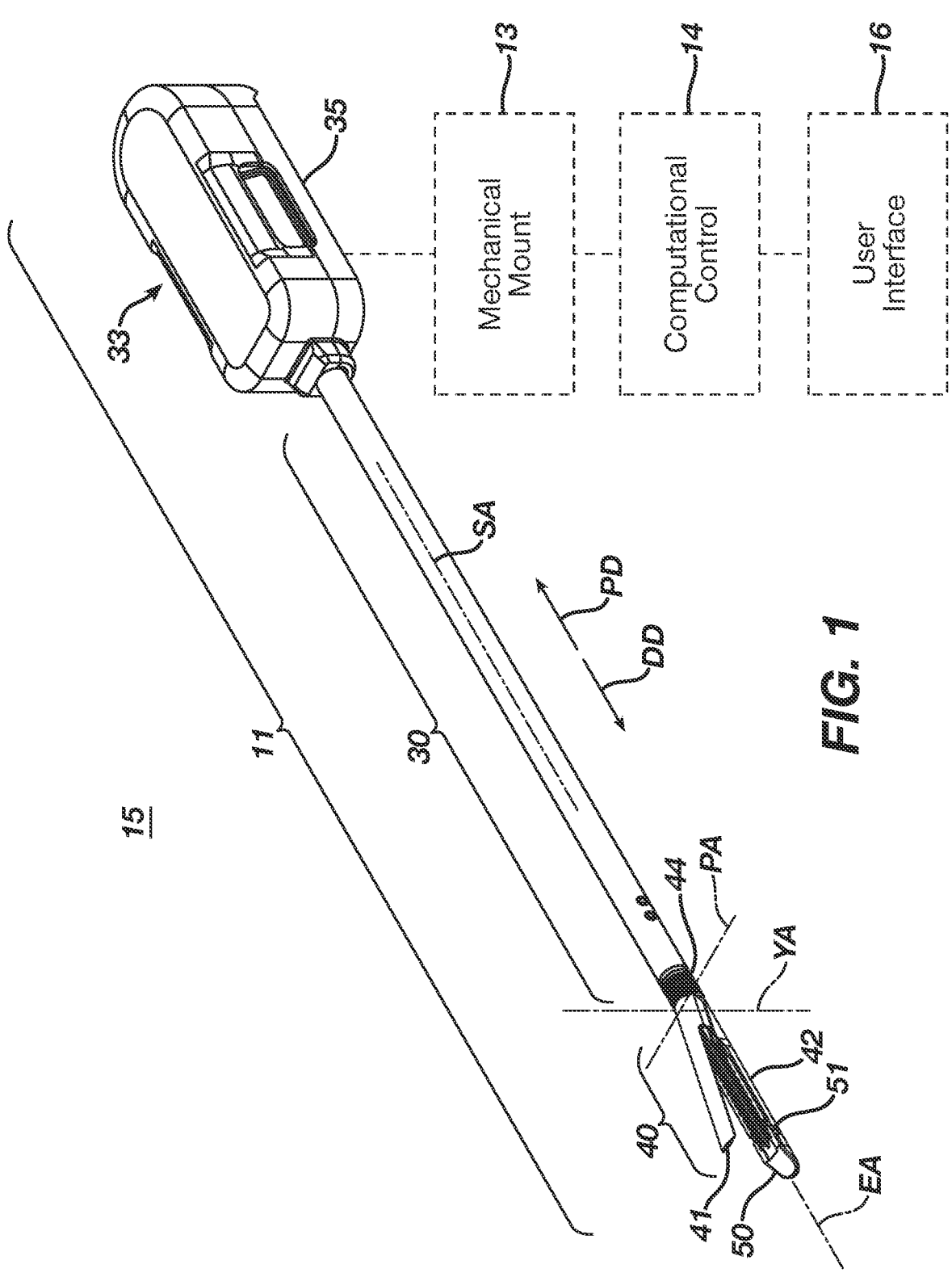
FIG. 1 is a perspective view of an exemplary surgical stapler tool of a robotic surgery system.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives, and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g., "about 90%" may refer to the range of values from 81% to 99%.

As used herein, the terms "patient," "host," "user," and "subject" refer to any human or animal subject and are not intended to limit the systems or methods to human use, although use of the subject invention in a human patient represents a preferred embodiment. As well, the term "proximal" indicates a location closer to the operator whereas "distal" indicates a location further away to the operator or physician.

As used herein, the term "memory" and "non-transitory computer-readable media" are used interchangeable and are understood to include, but are not limited to, random access memory (RAM), read-only memory (ROM), electronically erasable programmable ROM (EEPROM), flash memory or other memory technology, compact disc ROM (CD-ROM), digital versatile disks (DVD) or other optical storage, magnetic cassettes, magnetic tape, magnetic disk storage or other magnetic storage devices, or any other tangible, physical medium which can be used to store computer readable information.

Alternative apparatus and system features and alternative method steps are presented in example embodiments herein. Each given example embodiment presented herein can be modified to include a feature and/or method step presented with a different example embodiment herein where such feature and/or step is compatible with the given example as understood by a person skilled in the pertinent art as well as where explicitly stated herein. Such modifications and variations are intended to be included within the scope of the claims.

Knowing or being able to estimate tissue properties such as thickness is an unmet need in many surgical settings that can be utilized to more consistently make appropriate tissue-dependent treatment modalities. For instance, being able to estimate tissue thickness prior to stapler firing of a surgical stapler could assist surgeons/users in selecting the appropriate staple accessory (e.g., end effector or reload). More specifically, such a system deployed in a robotic system may be used to double check if the selected reload color is appropriate, and if any precautions (e.g., upsize reload) are needed before firing. Each staple cartridge reload can include staples with a height appropriate for tissue having the thickness indicated for use. The cartridge reloads can be color coded and otherwise configured to indicate a tissue thickness for use. As used herein, "color" can indicate size/type of staple/reload, and a change of "color" can indicate changing a reload or staple size. Such feature could enhance surgeons' decision-making and user experience during stapling. In addition, the estimated tissue thickness can be a critical input to the clamping and firing algorithms for developing intelligent/smart controls. FIGS. 10, 11, 12A, and 12B are flow diagrams illustrating aspects of example software algorithms, which are explained in greater detail hereinbelow.

Figure 2:
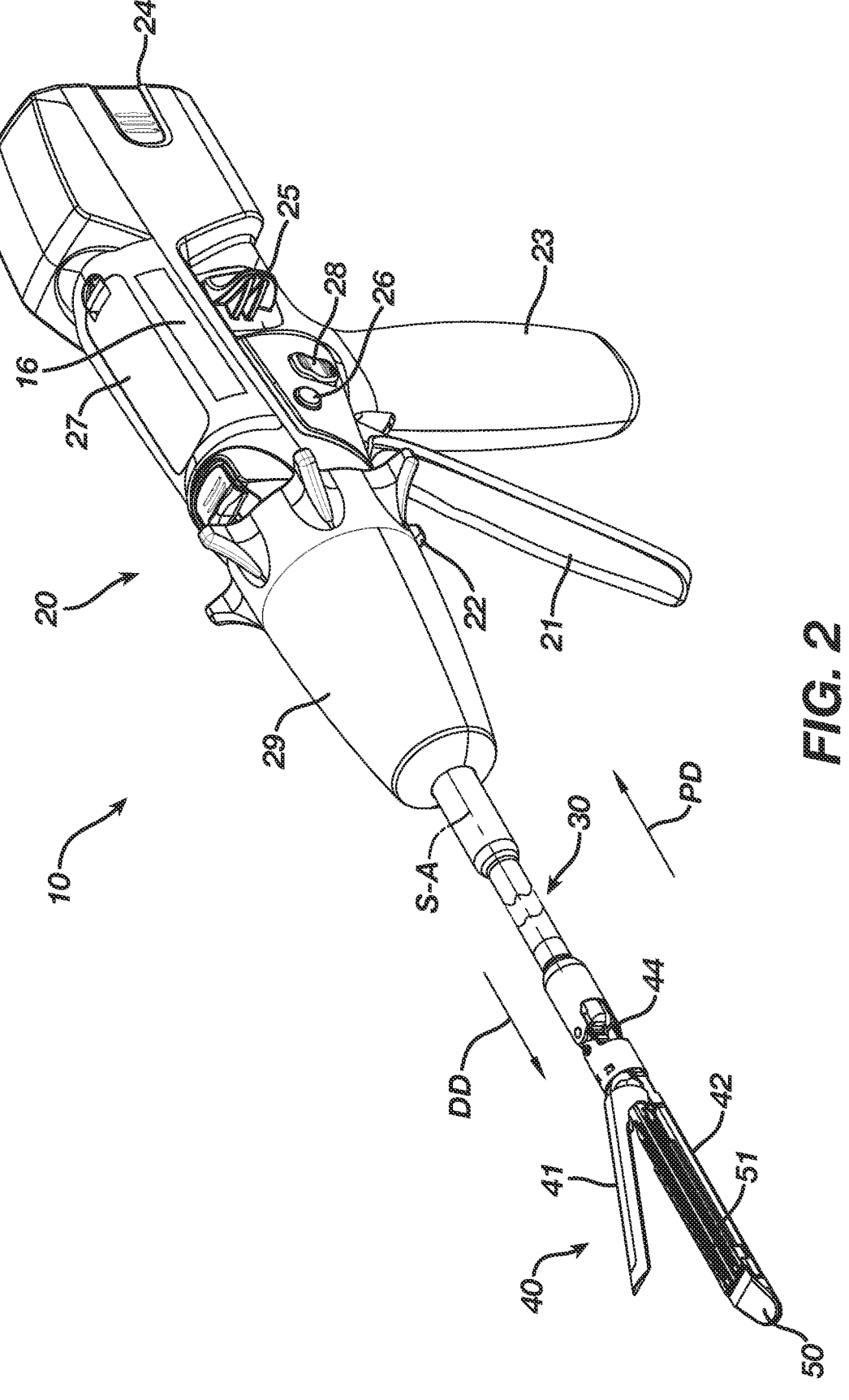
FIG. 2 is a perspective view of an exemplary handheld powered surgical stapler.
Figure 3:
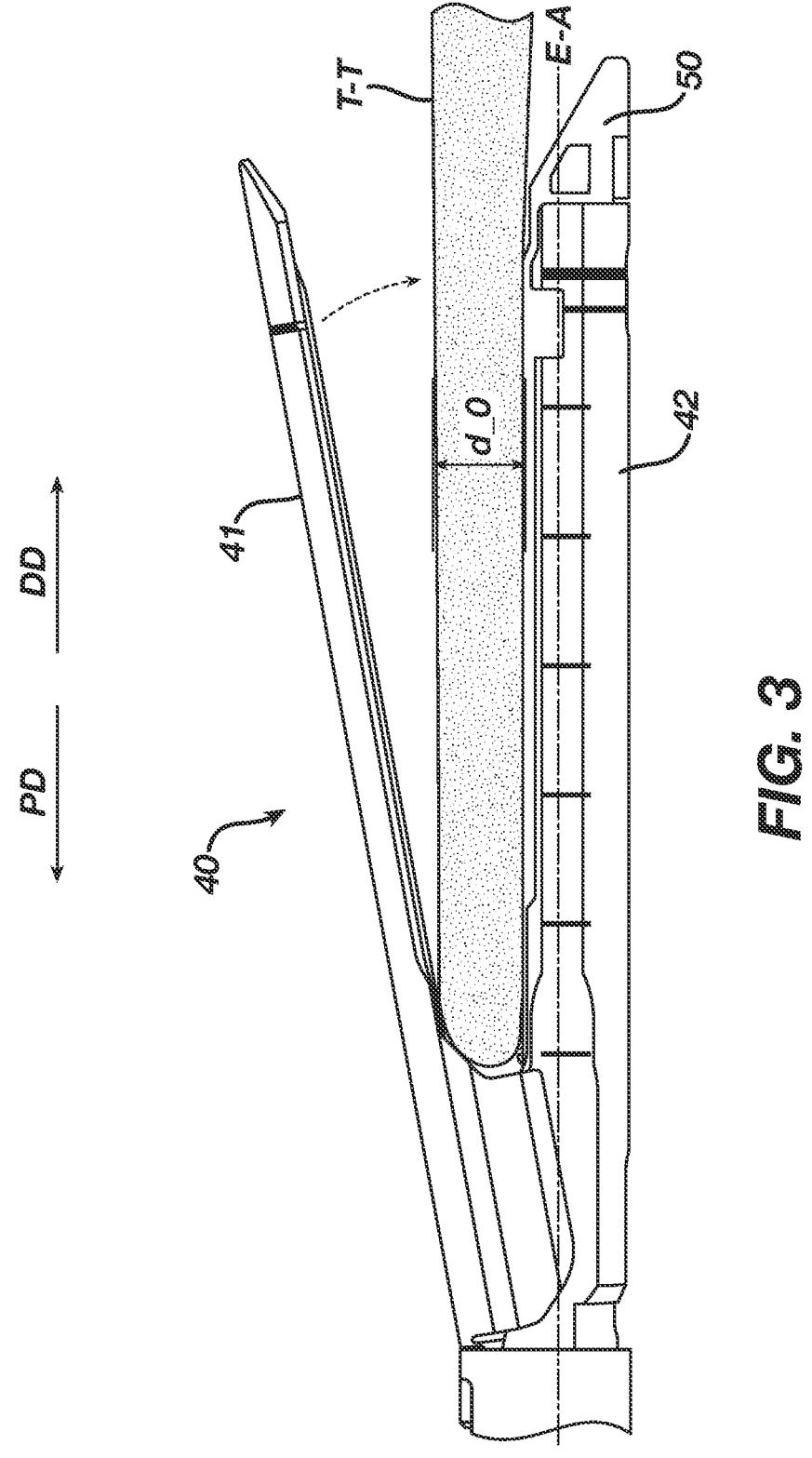
FIG. 3 is an illustration of an exemplary end effector of an exemplary powered surgical stapler prior to compression of tissue between jaws.
Figure 6:
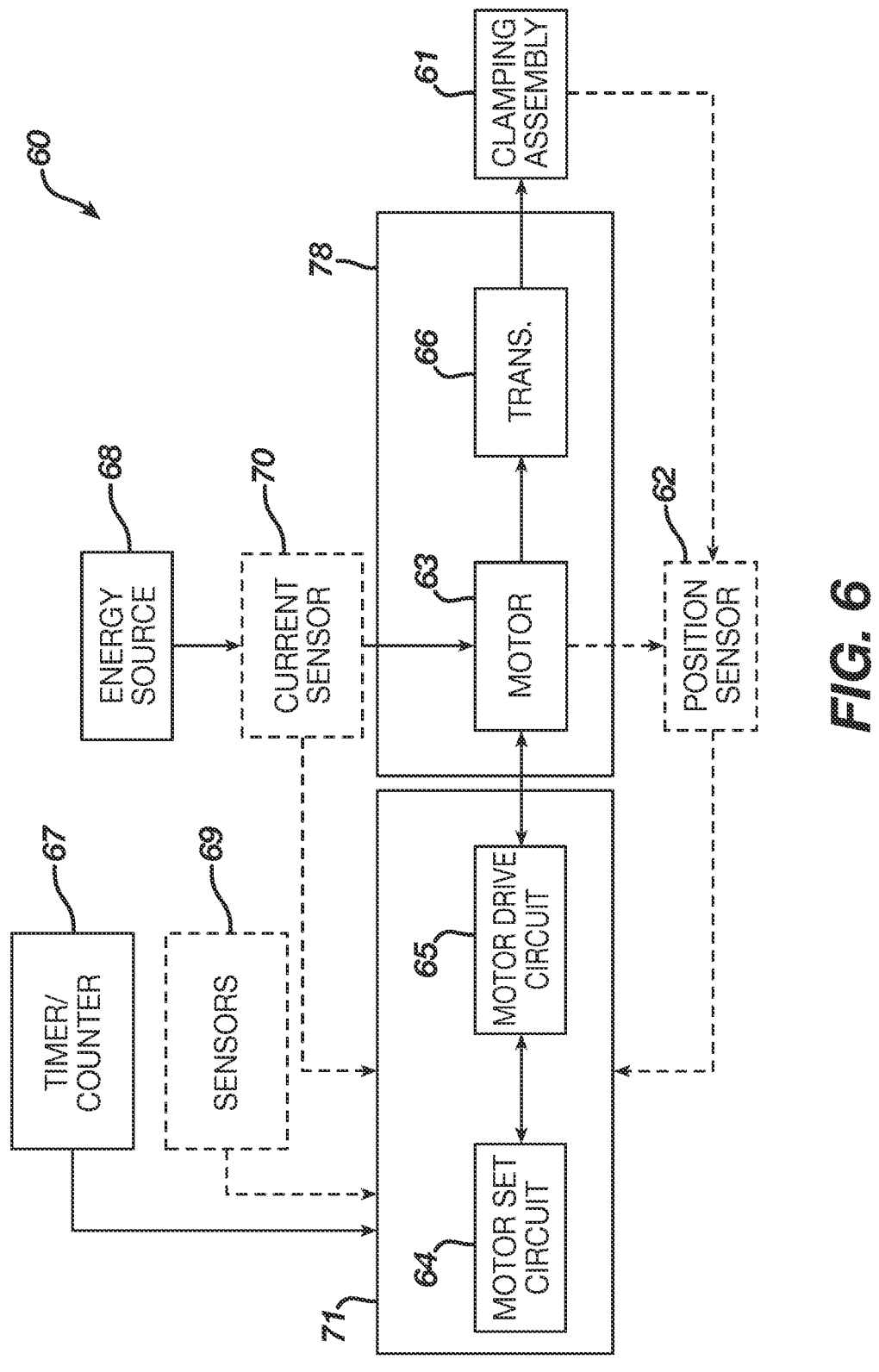
FIG. 6 is a block diagram of an exemplary end effector drive system for a powered surgical instrument.
Figure 7A:
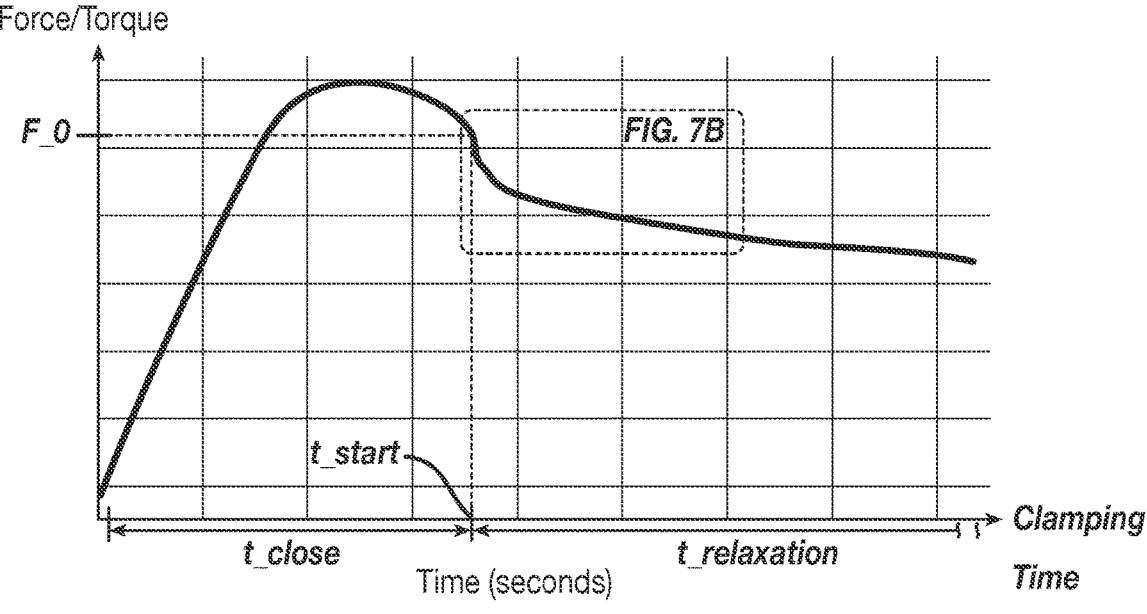
FIGS. 7A and 7B are illustrations of exemplary motor parameter as a function of time during clamping stages of an end effector.
Figure 7B:
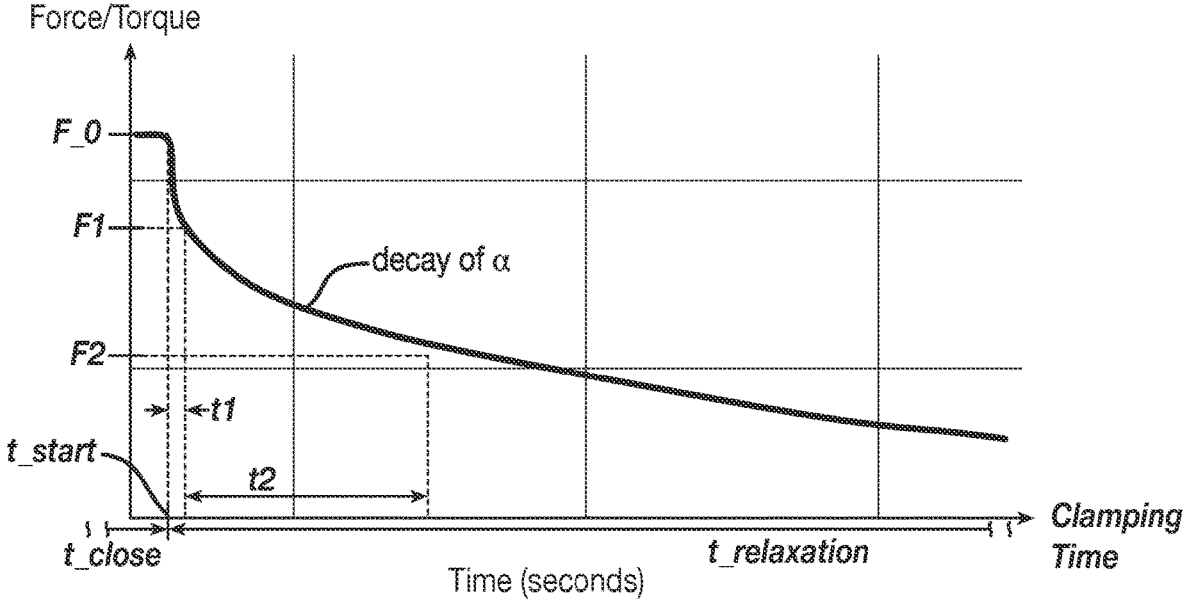
Figure 8:
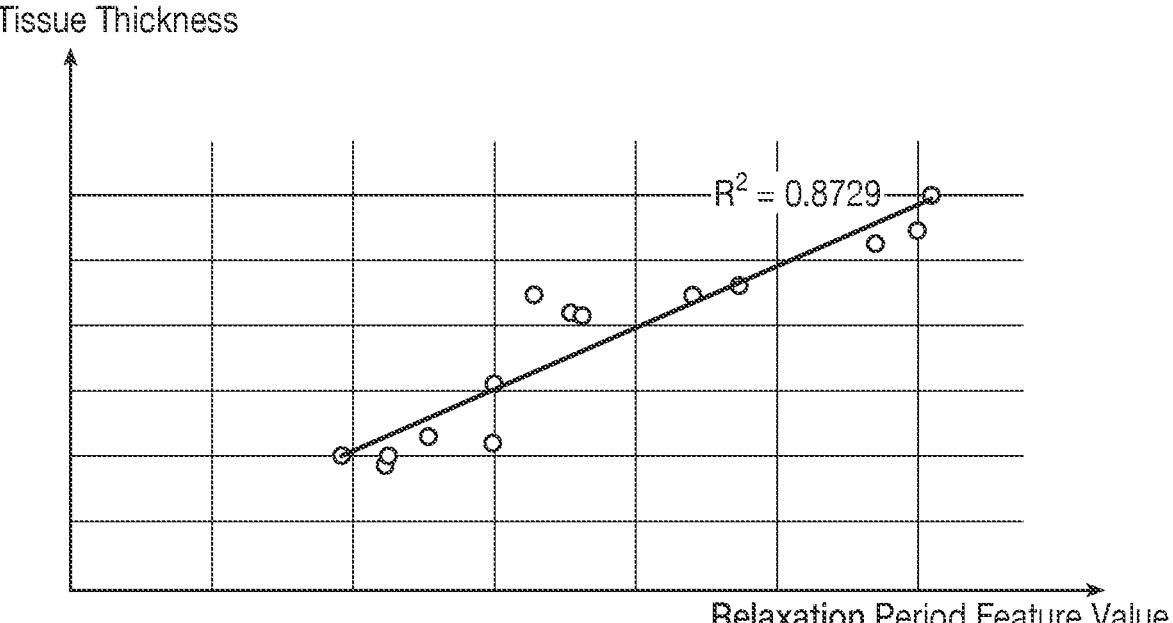
FIG. 8 is a graph illustrating a linear correlation between tissue thickness and the value of the mathematical feature during a relaxation time period.

Briefly summarizing, example surgical instruments presented herein generally include an end effector 40 configured to clamp tissue TT between jaws 41, 42 such that the tissue relaxes during a relaxation time period following closure of the jaws 41, 42. FIG. 1 is a perspective view of an exemplary surgical stapler tool 11 of a robotic surgery system 15 which can utilize the aforementioned software algorithms. FIG. 2 is a perspective view of an exemplary handheld powered surgical stapler 10 which can utilize the aforementioned software algorithms. FIG. 3 illustrates closure of the end effector 40 on tissue TT. FIGS. 4A, 4B, 5A, and 5B illustrate progression of tissue relaxation. FIG. 6 is a block diagram of an exemplary end effector drive system 60 for a powered surgical instrument. FIGS. 13, and 14A-14D illustrate additional aspects and examples of a surgical instrument which can utilize the aforementioned software algorithms. FIGS. 7A and 7B illustrate motor force/torque as a function of time during closure and tissue relaxation stages of an end effector as one illustrative example. Jaws close around tissue during the end effector closure time period t_close, and once the jaws are closed and in contact with tissue, tissue relaxes between the closed jaws during the tissue relaxation time period t_relaxation. In this example, mathematical feature (input), includes a maximum clamping torque/force F_0 during tissue relaxation, which occurs at the start of relaxation. Alternatively, the relaxation time period t_relaxation may include an initial transient time period t1, and a maximum clamping torque/force F1 can be measured after the initial transient time period t1. FIG. 8 shows a simple, but well correlated, linear correlation between the tissue thickness and this feature input F_0 (or F1), which shows the linear correlation from multiple powered surgical stapler tissue performance test datasets. In some examples, further enhancements to the relationship of tissue relaxation properties and tissue staple loads may be determined through the relaxation decay rate a to fit a more accurate tissue material viscoelastic property characteristics.

The resulting software algorithm may be effective at countering variability observed between tissue thickness and staple loads.

The method and concept demonstrated here could also be extended from stapler to other surgical instruments, such as Energy tools (e.g., Enseal™), which utilize a time-period of tissue clamping and relaxation between jaws during a surgical procedure. Example surgical instruments illustrated herein are not limiting, and aspects of the aforementioned software algorithms can be applied not only for surgical staplers and robotic systems, but for other systems involving powered clamping of tissue as understood by a person skilled in the pertinent art.

In some examples, a motor parameter such as motor torque, force, or speed characteristic is monitored during relaxation of tissue in the end effector, and a mathematical feature of the motor parameter is extracted and inputted to a pre-learned correlation model to estimate or predict the tissue thickness.

In some examples, the software algorithm predicts/estimates the tissue thickness during tissue relaxation stage, which is inputted to a computer logic to recommend the reload color/type and then compare with the existing installed reload type/color to confirm if an appropriate reload was selected. If not, the computer logic could suggest upsizing the reload based on predicted tissue thickness.

In some examples, computer logic guides the creation of "too thick tissue" warning feedback to the surgeons if the predicted tissue thickness exceeds a preset limit. An example warning message could be displayed on the instrument or system which reads "tissue is too thick to fire, please change another proper reload" or similar language.

In some examples, estimated tissue thickness from real-world surgical procedures can be collected by the computational system (e.g., processor and memory) of multiple surgical instruments over multiple surgical procedures to form a dataset that could be leveraged for next-generation smart instrument designs.

In some examples, post firing, and prior to tool removal for new cartridge insertion, the surgeon may target the next site and do a grasp including a tissue relaxation time period to extract the mathematical feature of the motor parameter to understand the recommended reload color to use for the next staple line.

In some examples, a surgeon may grasp along the tissue such that tissue relaxes and the mathematical feature of the motor parameter is extracted to build up a tissue profile map of the general site of interest to better understand the underlaying structure to allow for improved staple line outcome.

Examples are described in greater detail in relation to the figures.

FIG. 1 is a perspective view of an exemplary surgical stapler tool 11 of a robotic surgery system 15. The surgical stapler tool 11 can be mounted to a mechanical mount 13, such as robotic arm cart, which can be controlled by a computational control unit 14, such as a controller station, of a robotic surgical system 15. An example robotic surgical system is disclosed in U.S. Pat. No. 7,524,320, incorporated herein by reference. The surgical stapler tool 11 can be used with various alternative robotic surgical systems as understood by a person skilled in the pertinent art. The surgical stapler tool 11 can be modified for use with such robotic surgical systems as understood by a person skilled in the pertinent art.

The surgical stapler tool 11 includes a mounting portion 33 configured to mount to the mechanical mount 13 of the robotic surgical system 15. The mounting portion 33 includes a housing 35 covering mechanical mechanisms of the mounting portion 33 and configured to mate the mechanical mechanisms of the mounting portion 33 to the mechanical mount 13 of the robotic surgical system 15.

The surgical stapler tool 11 includes a shaft 30 that is sized, shaped, and otherwise configured to extend through a body opening of the patient. The end effector 40 is configured to deliver staples 51. The end effector 40 may also be configured to cut tissue within the body of the patient. The end effector 40 includes an anvil 41 and a staple jaw 42 opposite the anvil 41. The anvil 41 and staple jaw 42 are collectively referred to herein as "jaws." The staple jaw 42 can include a staple cartridge 50 (also referred to herein as a "reload" or "cartridge reload") containing the staples 51. The staple cartridge 50 can be replaceable. Alternatively, the end effector 40 may be replaceable. A replaceable staple cartridge or end effector is generally presented herein as examples of a "surgical stapling accessory".

The anvil 41 and staple jaw 42 are illustrated in an open position. The anvil 41 and staple jaw 42 can be moved toward each other to move the end effector 40 to a clamped configuration. The end effector 40 can be actuated to deploy staples 51 into tissue during a firing stroke. Rotation of the anvil 41 to clamp tissue and deployment of staples 51 during a firing stroke are respectively motor driven by one or more motors. In addition to, or as an alternative to deploying staples, the end effector 40 can deliver electrical energy (e.g., bipolar energy), friction (e.g., ultrasonic) or other electrically-driven energy source to seal tissue.

The computational control 14 is configured to actuate mechanisms of the mechanical mount 13, which in turn, positions the surgical stapler tool 11 and interface with mechanical controls of the mounting portion 33 of the surgical stapler tool 11 to operate the end effector 40. The surgical stapler tool 11 may be driven by one or more motors which may be located in the housing 35, the mechanical mount 13, or elsewhere in the robotic surgical system 15. Torque of motor(s) located outside of the mounting portion 33 are transmitted via the mechanical mount 13 to the mounting portion 33 of the surgical stapler tool 11 by mechanical interconnect(s) between the mechanical mount 13 and mounting portion 33. The torque of motor(s) within the mounting portion 33 and/or transmitted to the mounting portion 33 via the mechanical mount 13 are transmitted by elongated mechanical structures through the shaft 30 to the end effector 40.

The surgical stapler tool 11 may be purely mechanical or may include electronic components such as motors, processors, memory, etc.

Software to control tissue clamping by the end effector 40 can be stored in memory of the computational control 14 and/or in memory of the surgical stapler tool 11. The software can be configured to monitor an instrument parameter during a tissue relaxation time (t_relaxation) period and utilize the instrument parameter data for various instrument functions. For instance, the software can determine a total clamping time for tissue to relax to have subsequent successful firing stroke based on clamping force and/or torque of motor(s) driving the end effector 40 during clamping. The software can otherwise include instructions for operating the end effector 40 as described in greater detail elsewhere herein.

The surgical stapler tool 11 further includes an articulation joint 44 between the shaft 30 and the end effector 40. The articulation joint 44 is configured to permit the end effector 40 to be angled in relation to a longitudinal axis S-A of the shaft 30. As illustrated, the end effector 40 has a longitudinal axis EA that is aligned with the shaft axis S-A. The articulation joint 44 can be bent so that the end effector axis EA is angled toward a pitch axis PA, yaw axis YA, or some combination thereof. The articulation joint 44 can be bent manually by pressing the end effector 40 against tissue or other object or powered via one or more motor(s) of the robotic surgical system 15. Additionally, or alternatively, the articulation joint 44 can be powered by the same or different motor configured to actuate clamping and/or firing of the end effector 40.

The robotic surgical system 15 further includes a user interface 16. The robotic surgical system 15 may be configured to provide tissue property information in real time to the user interface 16. The robotic surgical system 15 may be configured to provide a recommendation for end effector 40, cartridge 50 or other surgical stapling or treatment modality accessory at the user interface 16. Additionally, or alternatively, the robotic surgical system 15 may be configured to provide a user alert to the user interface 16 indicating that the installed surgical stapling accessory, such as end effector 40 or cartridge 50, is incompatible with tissue grasped by the pair of jaws 41, 42 of the end effector 40.

The surgical stapler tool 11 can be modified to provide additional or alternative therapeutic treatments involving clamping tissue by the end effector 40. For instance, the end effector 40 can be modified to include electrodes configured to delivery thermal treatment to tissue in addition to, or in lieu of staples 51. The modified surgical stapler tool 11 can be driven by software including methods for monitoring forces/torques response characteristics while tissue relaxes between clamped jaws, assuming the forces/torques experienced during jaw closure can be measured/monitored in real-time.

FIG. 2 is a perspective view of an exemplary handheld powered surgical stapler 10 including a handle 20, a shaft 30, and an end effector 40. The handle 20 is configured to be grasped, manipulated, and actuated by a clinician. The shaft 30 is sized, shaped, and otherwise configured to extend through a body opening of the patient. The end effector 40 is configured to deliver staples 51. The end effector 40 may also be configured to cut tissue within the body of the patient. The end effector 40 and shaft 30 of the handheld powered surgical stapler 10 illustrated in FIG. 2 can be configured similar to the end effector 40 and shaft of the surgical stapling tool 11 illustrated in FIG. 1.

The handle 20 can include a closure trigger 21, a firing trigger 22, and a grip 23 sized such that a clinician can single-handedly hold the handheld powered surgical stapler 10 by the grip 23 while manipulating the closure trigger 21 or the firing trigger 22. The closure trigger 21 is operably connected to a motor disposed within the handle 20 such that when the closure trigger 21 is pulled, the motor is driven to cause the end effector 40 to clamp tissue. The firing trigger 22 is operably connected to a motor disposed within the handle 20 such that when the firing trigger 22 is pulled, the motor is driven to cause the end effector 40 to deploy staples 51 into the clamped tissue and may also cut the clamped tissue. The closure trigger 21 and the firing trigger 22 can be coupled to separate respective motors, or the same motor.

The handle 20 can further include additional features such as a firing trigger lock mechanism (not illustrated) which can be manipulated to prevent actuation of the firing trigger 22, a power pack 24 configured to provide electrical power to the motor and other electrical components of the handheld powered surgical stapler 10, a closure release button 25 which can be manipulated to release the end effector 40 and the closure trigger 21 from the clamped position, a home button 26 that can be pressed to cause the motor to move a firing assembly in the proximal direction PD to a home position, a manual override 27 including a mechanical actuator which can be manipulated to mechanically move the firing assembly proximally to the home position, articulation button 28 that can be pressed to cause a motor to articulate the end effector 40 at an articulation joint 44 so that the end effector 40 is at an angle with a longitudinal axis S-A of the shaft 30, a rotatable nozzle 29 configured to be rotated so that the shaft 30 and end effector 40 rotate about the shaft longitudinal axis S-A, a display 16 configured to display information related to the handheld powered surgical stapler 10, variations thereof, other compatible features of a powered surgical stapler handle 20, and combinations thereof.

The end effector 40 includes an anvil 41 and a staple jaw 42 opposite the anvil 41. The anvil 41 and staple jaw 42 are illustrated in an open position. The anvil 41 and staple jaw 42 can be moved toward each other to move the end effector 40 to a clamped configuration. For instance, tissue (not illustrated) can be positioned between the anvil 41 and staple jaw 42 in the open position, and the anvil 41 can rotate toward the staple jaw 42 to clamp the tissue.

When the end effector 40 is in the clamped configuration, the firing trigger 22 can be pulled to cause deployment of staples 51 from the cartridge 50 and may also cause cutting of tissue.

Software to control tissue clamping by the end effector 40 can be stored in memory of the handheld powered surgical stapler 10.

Portions of the handheld powered surgical stapler 10 may be detachable and interchangeable. Staples 51 may be housed in a staple cartridge 50 that is detachable from the end effector 40. The end effector 40 may be detachable from the shaft 30, and the shaft 30-handle 20 combination may be configured for use in connection with interchangeable end effectors. At least a portion of the shaft 30 including the end effector 40 may be detachable from the handle 20, and the handle 20 may be configured for use in connection with interchangeable shaft assemblies having different shaft lengths and/or different end effectors attached thereto.

FIG. 3 is an illustration of an exemplary end effector 40 of an exemplary powered surgical stapler prior to compression of tissue TT between jaws. The end effector 40 can be configured for a robotic surgical system such as illustrated in FIG. 1, or a handheld surgical stapler such as handheld powered surgical stapler 10 illustrated in FIG. 2. The end effector 40 generally presents an example end effector of a surgical instrument configured for compression of tissue. The end effector 40 need not deploy staples and may be adapted for transection, suturing, cauterization, temporary tissue clamping (e.g., graspers, bipolar, etc.), or other operations as understood by a person skilled in the pertinent art. The end effector 40, modified for alternative applications, may be configured for use with a robotic surgical system and/or handheld surgical device as understood by a person skilled in the pertinent art. For instance, the end effector 40 can be modified to include electrodes configured to delivery thermal treatment to tissue in addition to, or in lieu of staples 51. The end effector 40 can be driven by software including methods for monitoring a motor parameter (e.g., force, torque, or speed) characteristics during jaw clamping (e.g., while tissue relaxes between clamped jaws), assuming the forces/torques experienced during jaw closure and/or tissue relaxation can be measured/monitored in real-time.

The staple jaw 42 of the end effector 40 is aligned along a longitudinal axis E-A of the end effector 40. The tissue has an initial thickness d_0 prior to being clamped. The rotation of the anvil 41 toward the staple jaw 42 is motor driven.

Figures 4A, 4B:
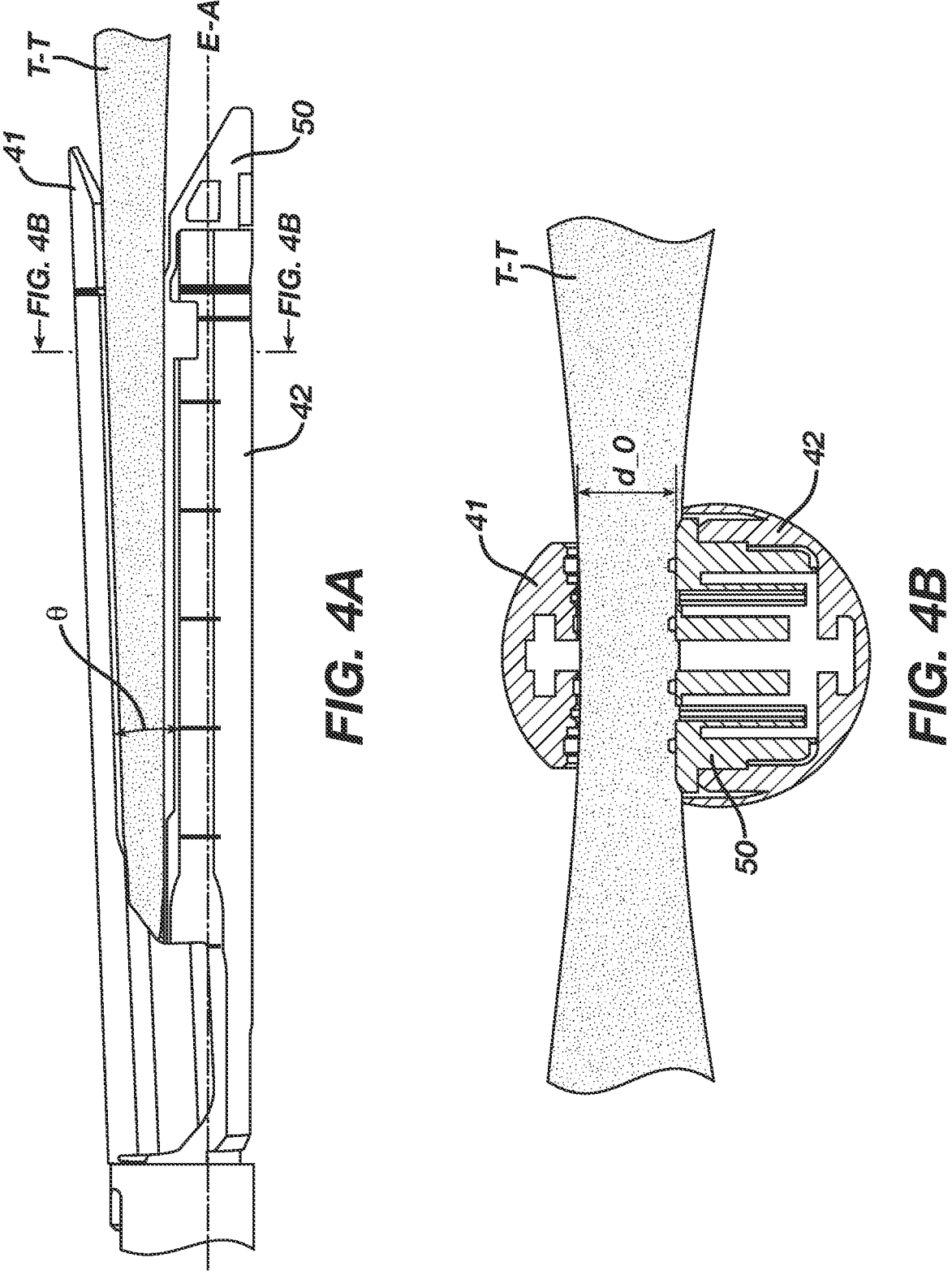
FIGS. 4A and 4B are illustrations of the exemplary end effector at an early stage of compression of tissue between the jaws.

FIGS. 4A and 4B are illustrations of the exemplary end effector 40 at an early stage of compression of tissue TT between the anvil 41 and staple jaw 42. FIG. 4B is a cross-sectional view through the anvil 41, staple jaw 42, and tissue TT as indicated in FIG. 4A. As the anvil 41 is rotated by motor torque/force toward the staple jaw 42 during the relaxation time, the tissue TT is compressed. The tissue thickness d_1 at an early stage of the relaxation time period is less than the initial thickness d_0.

Figure 5A:
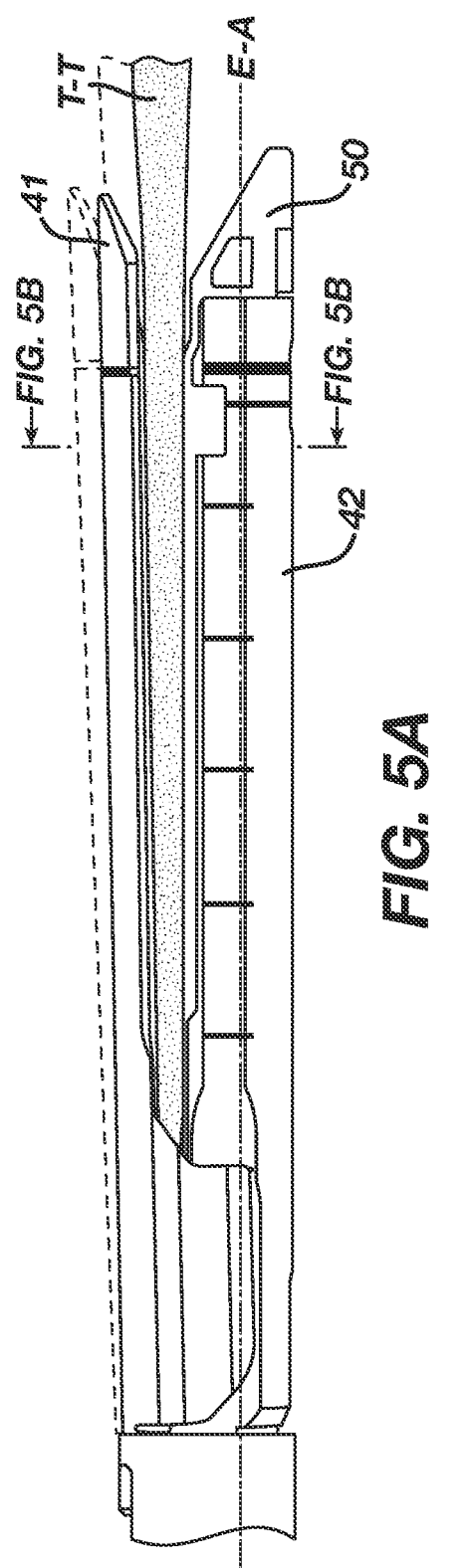
FIGS. 5A and 5B are illustrations of the exemplary end effector at the end of the relaxation time period.
Figure 5B:
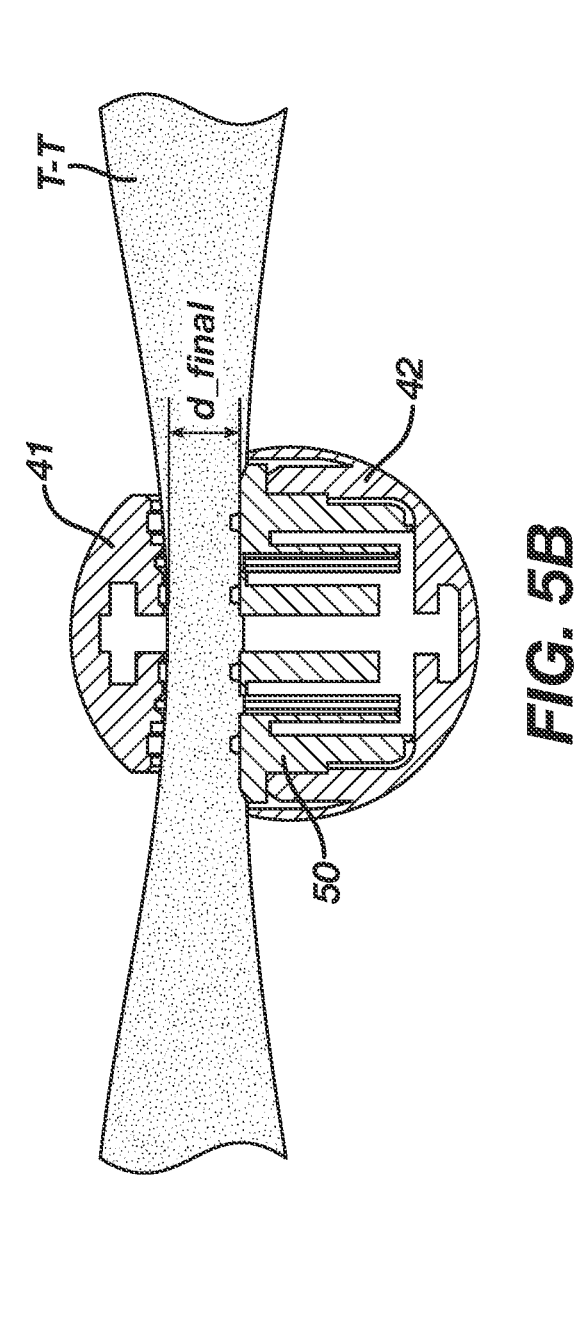

FIGS. 5A and 5B are illustrations of the exemplary end effector 40 at the end of the relaxation time period. The tissue thickness d_final at the end of the relaxation time period is reduced so that subsequent surgical operations can be performed, such as initiating a firing stroke of a surgical stapler. In the illustrated example, the final tissue thickness d_final is approximately 0.5 mm less than the initial tissue thickness d_0 prior to the relaxation time period as measured approximate a distal end of the treated tissue in the end effector 40.

FIG. 6 is a block diagram of an exemplary end effector drive system 60 for a powered surgical instrument. The end effector drive system 60 is configured to perform powered actuation of the end effector 40, including clamping of tissue. The end effector drive system 60 is configured to actuate the clamping assembly 61 to close the jaws 41, 42 of the end effector 40 illustrated in FIG. 3 and variations thereof as described herein and otherwise understood by a person skilled in the pertinent art. The end effector drive system 60 may further be configured to perform powered actuation of additional surgical operations of the end effector 40 such as driving a firing assembly to deploy staples 51.

The end effector drive system 60 includes a motor control circuit 71 configured to drive a motor 63. The end effector drive system 60 includes a transmission 66 configured to convert the rotational movement of a rotor of the motor 63 into longitudinal movement of a clamping assembly 61. The motor 63 and transmission 66 are collectively referred to herein as a motor assembly 78. Examples of clamping assemblies 61 are illustrated in FIGS. 13, and 14A-14D.

Figure 13:
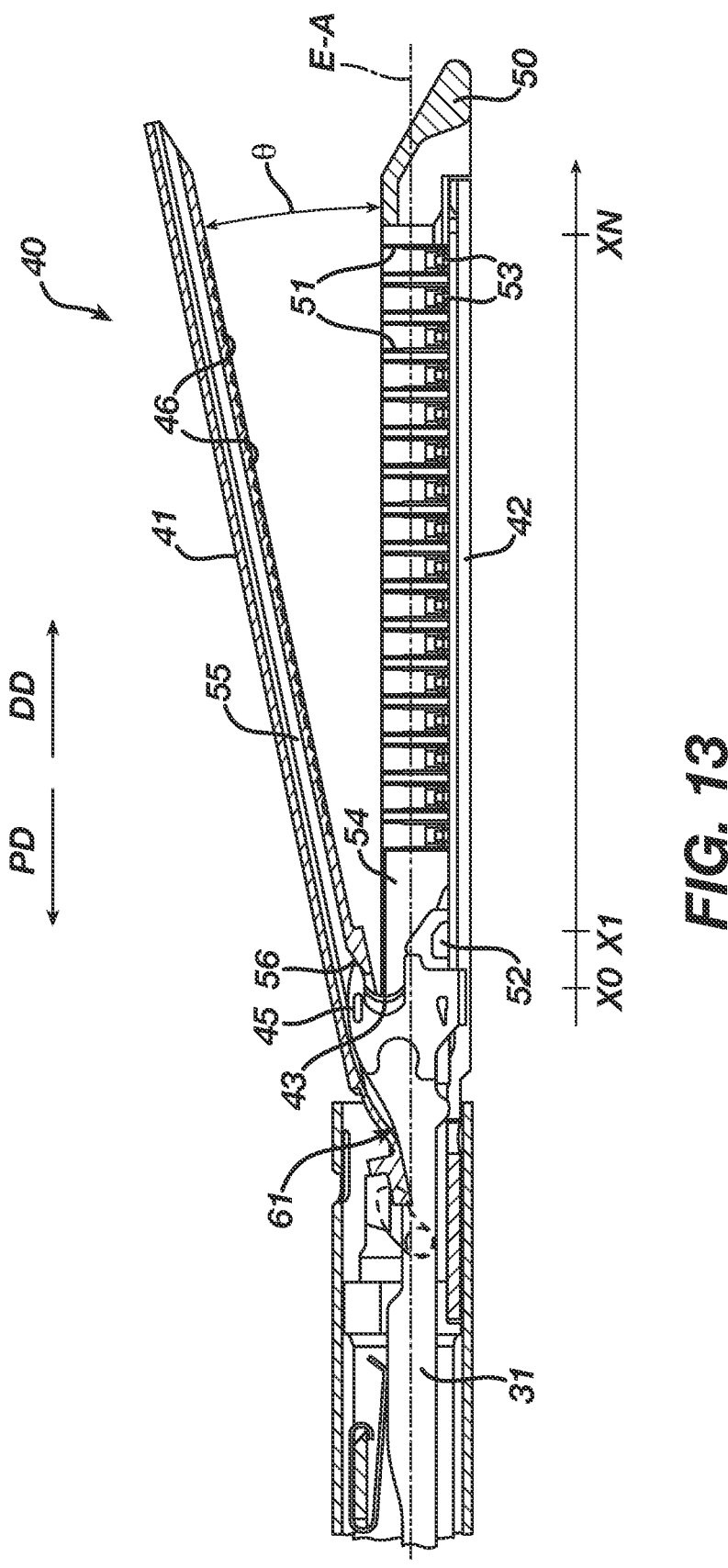
FIG. 13 is an illustration of a sectional view of the end effector 40.

In some examples, closing, clamping, and firing of the end effector 40 are actuated by the same motor 63 and common mechanical features, which can include an I-beam 45 (FIGS. 13, and 14A-14D) coupled to an elongated firing bar 31 (FIG. 13). The I-beam functions as a firing driver, and alternative firing driver configurations can be utilized as understood by a person skilled in the pertinent art. In such examples, the clamping assembly 61 is also referred to as a firing driver, firing assembly, or a clamping/firing assembly. Alternatively, closing and clamping firing are actuated by a separate motor than firing, and the assemblies for each have distinct mechanical features. In some examples, the end effector drive system 60 is not configured for firing. Note that the motor 63 as illustrated, may represent more than one motor. The position, movement, displacement, and/or translation of one or more components of the clamping assembly 61, can be measured by one or more position sensors 62. The position sensor(s) 62 may be configured to detect movement of the clamping assembly 61 and/or rotation of the rotor of the motor 63. The position sensor(s) 62 can additionally or alternatively be configured to sense displacement of a clamping/firing assembly during a firing stroke.

The motor control circuit 71 is illustrated as including a motor set circuit 64 and motor drive circuit 65, which are illustrated as two separate blocks. The motor set circuit 64 and motor drive circuit 65 may be separate circuits or may be integrated as a single circuit. The motor set circuit 64 is configured to provide a motor setpoint signal output to the motor drive circuit 65. The motor setpoint signal is indicative of a target parameter, such as a target speed of the clamping assembly 61. The motor drive circuit 65 is configured to provide a motor drive signal to the motor 63 such that the motor drive signal is based on the motor setpoint signal and intended to drive the motor 63 so that the clamping assembly 61 is driven to the target parameter.

The motor set circuit 64 and the motor drive circuit 65 may include one or more processors and memory (i.e., one or more non-transitory computer-readable medium) with instructions that can be executed by the one or more processors to cause the motor set circuit 64 and the motor drive circuit 65 to drive the motor 63. The motor set circuit 64 and/or motor drive circuit 65 can include a feedback controller, which can be one of any feedback controllers, including, but not limited to a PID, a State Feedback, LQR, and/or an Adaptive controller, for example. The motor set circuit 64 and/or motor drive circuit 65 can include a power source to convert the signal from the feedback controller into a physical input such as a constant voltage, pulse width modulated (PWM) voltage, frequency modulated voltage, current, torque, and/or force, for example.

The motor control circuit 71 configured to electrically drive the motor 63 during a relaxation time period, monitor a motor parameter of the motor 63 during at least a portion of the relaxation time period, extract a mathematical feature of the motor parameter during at least a portion of the relaxation time period, and determine a treatment modality based at least in part on the mathematical feature. The motor parameter can include a speed, torque and/or force of the motor 63. The motor torque, force, or speed can be used to determine a treatment modality such as selection of a stapling accessory (e.g., cartridge reload or end effector).

FIG. 7A is a graph illustrating a motor parameter that includes motor force and/or motor torque during a closing time period t_close and a tissue relaxation time period relaxation. FIG. 7B is a zoomed view of a portion of the graph as indicated in FIG. 7A. The chart assumes that clamping force and motor torque are related. The chart presents an embodiment in which the motor parameter is motor torque. Motor torque may be measured directly (e.g., by torque sensors) or indirectly (e.g., calculated based on motor speed and power) as understood by a person skilled in the pertinent art. Alternatively, clamping force may be measured directly or determined by some other motor parameter which correlates to clamping force.

Referring collectively to FIGS. 6, 7A, and 7B, in some examples, the motor control circuit 71 is configured to electrically drive the motor 63 translating a firing driver or firing assembly including an I-beam 45 (FIG. 13) distally to close the jaws 41, 42 of an end effector 40 on tissue TT during the closure time period t_close, then allow the tissue TT to relax between the jaws during the relaxation time period t_relaxation. The motor control circuit 71 can be configured to determine a point in time in which the jaws have completed the closure time period t_close and began the relaxation time period t_relaxation. In some examples, the motor control circuit 71 is configured to extract the mathematical feature F_0 at the beginning of the relaxation time period t_relaxation, which can be a singular predetermined time, and determine the treatment modality based on the extracted mathematical feature F_0. The start time t_start of the relaxation time period t_relaxation can occur when the pair of jaws 41, 42 are closed to a predetermined angle Θ (FIG. 4A). Alternatively, the relaxation time period t_relaxation may include an initial transient time period t1, and a maximum clamping torque/force F1 can be measured after the initial transient time period t1.

Additionally, or alternatively, the motor control circuit 71 is configured to extract a time constant α of an exponential decay model of the motor parameter during a predictive portion t2 of the clamping/relaxation time period. The mathematical feature used to determine treatment modality can include the time constant α and/or the time constant α can be supplemental to the mathematical feature. In some examples, the motor control circuit 71 is configured to determine the treatment modality based at least in part on the time constant α.

FIG. 8 is a graph illustrating a linear correlation between tissue thickness and the value of the mathematical feature during the relaxation time period (Relaxation Period Feature Value). Referring collectively to FIGS. 6 and 8, the linear correlation can be pre-built through a calibration process in which the motor control circuit 71, or similar motor control circuit, is used to drive a firing driver to close and clamp jaws of an end effector on tissue, extract the mathematical feature during the relaxation time period, and measure the resulting tissue thickness. Multiple clamping events can be plotted, and a linear correlation can be fit to the plot. The resulting linear correlation can be used in software of the surgical instrument so that the motor control circuit 71 compares a mathematical feature (extracted during a relaxation time period when clamping a tissue of unknown thickness) to the linear correlation and uses that comparison to determine the tissue thickness of the clamped tissue. In such examples, the motor control circuit 71 is configured to compare the mathematical feature F_0, α to a linear correlation to tissue thickness.

Still referring to FIGS. 6 and 8, in some examples, the treatment modality determined by the motor control circuit 71 can include utilization of a surgical stapling accessory (e.g., end effector 40, staple cartridge 50) indicated for use on a predetermined tissue thickness. The motor control circuit 71 can be configured to identify the predetermined tissue thickness for selection of the surgical stapling accessory. In some examples, the correlation model used by the motor control circuit 71 is based on data collected from use of a plurality of surgical stapling accessories indicated for use on disparate predetermined tissue thickness. For instance, during the calibration process, surgical staplers having a variety of sized cartridge reloads or end effectors indicated for use on disparate tissue thicknesses can be used to build the linear correlation model. This linear correlation model based on the plurality of surgical stapling accessories indicated for use on disparate predetermined tissue thickness can then be used by the motor control circuit 71 to determine tissue thickness when clamping tissue of unknown thickness.

Alternatively, the motor control circuit 71 can utilize a correlation model based on data collected from use of a plurality of surgical stapling accessories indicated for use on a predetermined thickness consistent with a predetermined thickness indication for an installed surgical stapling accessory of the surgical instrument (e.g., handheld powered surgical stapler 10, surgical stapler tool 11). Meaning, the motor control circuit 71 can be provided with, or be configured to determine information about, an installed surgical stapling accessory that is indicated for use on a tissue with a predetermined thickness (e.g., within a range of thicknesses), and the motor control circuit 71 can utilize a corresponding linear correlation based on calibration for uses of stapling accessories similar to the installed surgical stapling accessory such as the end effector 40 and the staple cartridge 50 (e.g., indicated for use on the same predetermined tissue thickness as the installed surgical stapling accessory). As such, the motor control circuit 71 can be configured to compare the mathematical feature F_0, α to a correlation model. The comparison may be based on data collected from use of a plurality of surgical stapling accessories such as the end effector 40 and the staple cartridge 50 indicated for use on a predetermined thickness, which is consistent with a predetermined thickness indication for an installed surgical stapling accessory 40, 50 of the surgical instrument 10, 11.

The motor control circuit 71 can be configured to determine tissue thickness based at least in part on an expected thickness after compression d_final (FIG. 5B). Additionally, or alternatively, the motor control circuit 71 is configured to determine tissue thickness based at least in part on the expected thickness d_final after approximately 15 seconds of compression of the tissue with an applied pressure of approximately 8 g/mm$^2$. Additionally, or alternatively, the motor control circuit 71 is configured to determine tissue thickness based on techniques appropriate for a treatment modality indicated for use on tissue having a certain thickness as understood by a person skilled in the pertinent art.

In some examples, the control circuit 71 is configured to determine, based at least in part on the mathematical feature F_0, α, a tissue property including a thickness and/or tissue tension. The motor control circuit 71 can be configured to determine that the tissue property is undesirable and provide a user indication representing the undesirable tissue property. For instance, the tissue may be too thick or too thin to perform a procedure with the surgical instrument, or the treatment modality (e.g., cartridge reload) may not be appropriate for the tissue thickness. As another example, the tissue property may be such that additional precautions are required to perform a procedure such as additional tissue relaxation time or an adjusted treatment is required. The motor control circuit 71 can be configured to provide the determination of the tissue property in real time to a user interface 16. The real time determination can be used by a physician to make further determinations regarding the application of a treatment to select a more appropriate surgical instrument, select a more appropriate accessory, select a treatment modality, etc. In some examples, the control circuit 71 is configured to provide additional information to the user interface 16 (FIGS. 1 and 2) in this regard.

In some examples, the motor control circuit 71 is configured to retain data related to the tissue property from multiple clamping events during a surgical procedure. The motor control circuit 71 can be configured to build a tissue profile map based at least in part on the retained data from multiple clamping events. The tissue profile map can indicate tissue thickness at multiple locations in a treatment area. The motor control circuit 71 can be configured to display the tissue profile map on a display of the user interface 16 (FIGS. 1 and 2).

Figure 9A:
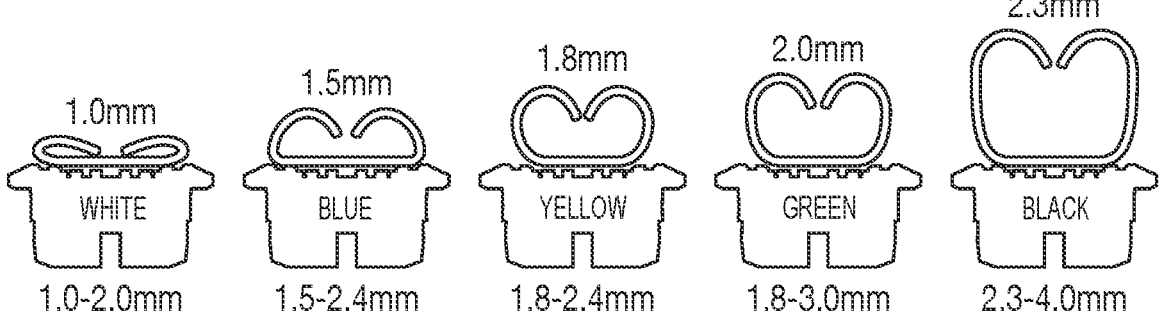
FIGS. 9A and 9B are exemplary staple cartridge reloads indicated for use with tissue having a thickness within a predetermined range of thicknesses.
Figure 9B:
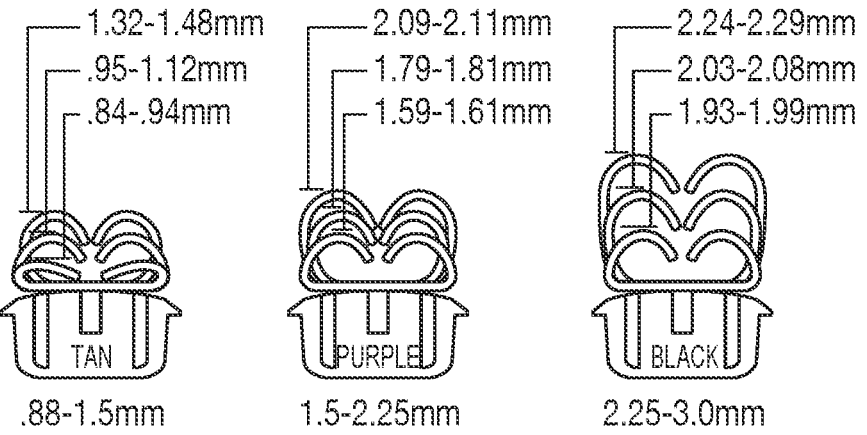

FIGS. 9A and 9B include examples of staple cartridge reloads indicated for use with tissue having a thickness within a predetermined range of thicknesses. Each staple cartridge reload includes staples with a height appropriate for tissue having the thickness indicated for use. The cartridge reloads can be color coded and otherwise configured to indicate a tissue thickness for use. The tissue thickness indicated for use can correspond to a formed staple height as illustrated. In FIG. 9A, a white cartridge is indicated for use for tissue between 1 and 2 mm thick and has a staple height of 1 mm; a blue cartridge is indicated for use for tissue between 1.5 and 2.4 mm thick and has a staple height of 1.5 mm; a yellow cartridge is indicated for use for tissue between 1.8 and 2.4 mm and has a staple height of 1.8 mm; a green cartridge is indicated for use for tissue between 1.8 and 3.0 mm and has a staple height of 2.0 mm; and a black cartridge is indicated for use for tissue between 2.3 and 4 mm and has a staple height of 2.3 mm. In FIG. 9B, a tan cartridge is indicated for use for tissue between 0.88 and 1.5 mm thick and has a short staple height of between 0.84 and 0.94 mm, a medium staple height of between 0.95 and 1.12 mm, and a tall staple height of between 1.32 and 1.48 mm; a purple cartridge is indicated for use for tissue between 1.5 and 2.25 mm thick and has a short staple height of between 1.59 to 1.16 mm, a medium staple height of between 1.79 and 1.81 mm, and a tall staple height of between 2.09 and 2.11 mm; and a black staple cartridge is indicated for use for tissue between 2.25 and 3 mm thick and has a short staple height of between 1.93 and 1.99 mm, a medium staple height of between 2.03 and 2.08 mm, and a tall staple height of between 2.24 and 2.29 mm. The staples in the cartridges in FIG. 9B are oriented in three rows parallel to the longitudinal axis of the end effector E-A with the tall staples being furthest from the center of the cartridge, outer rows, and the shortest staples being in a row closest to the center of the cartridge, inner rows.

Each cartridge reload illustrated in FIGS. 9A and 9B is an example of a treatment modality that is dependent on properties of the tissue. The cartridge reload is also an example of a stapling accessory that is indicated for use on a predetermined tissue thickness. Another example of a stapling accessory that is indicated for use on a predetermined tissue thickness may utilize the staples and predetermined tissue thickness as illustrated in FIGS. 9A and 9B but be housed in a disposable end effector rather than a cartridge reload. In the field of surgical staplers, the tissue thickness may be determined based at least in part on the thickness of tissue after approximately 15 seconds of compression with an applied pressure of approximately 8 g/mm². Using prior systems and methods, a physician estimates the tissue thickness based on visual and/or manual inspection and selects a stapling accessory accordingly. In some examples, systems and methods disclosed herein can utilize a mathematical feature of a motor parameter during a clamping time period (specifically during a tissue relaxation time period) to make a determination about tissue thickness and therefore appropriate stapling accessory selection. As illustrated in FIGS. 9A and 9B and understood by a person skilled in the art, in order to select an appropriate treatment modality (e.g., a right color cartridge), the determination of tissue thickness is not necessarily an exact or accurate one but could be an estimation or an approximate value instead.

Referring again to FIG. 6, in some examples, the motor control circuit 71 can be configured to make a selection of a surgical stapling accessory and provide a recommendation for the selected surgical stapling accessory at a user interface 16 (FIGS. 1 and 2). The control circuit 71 can be configured to receive data indicating the predetermined thickness that an installed surgical stapling accessory (e.g., the end effector 40 or the staple cartridge 50 as illustrated in FIGS. 1 and 2) is used for, and determine that the installed surgical stapling accessory is incompatible with tissue grasped by the pair of jaws 41, 42 of the end effector 40. For instance, during usage, a physician may first estimate tissue thickness based on visual or manual inspection, install a stapling accessory based on their estimation, and engage the surgical instrument (e.g., handheld powered surgical stapler 10 or surgical stapler tool 11 as illustrated in FIGS. 1 and 2) to close the jaws 41, 42 of the end effector 40 on tissue TT and clamp the tissue TT. The control circuit 71 can determine whether or not the installed stapling accessory is appropriate based on a mathematical feature of a motor parameter during the clamping time period (preferably during a tissue relaxation time period), and provide an indication of the appropriateness of the installed stapling accessory to the physician by providing a visual or audible indication via the user interface 16. If the control circuit 71 determines that the installed surgical stapling accessory (e.g., either the end effector 40 or the staple cartridge 50) is incompatible with the tissue TT grasped by the pair of jaws 41, 42 of the end effector 40, the motor control circuit 71 can be configured to provide a user an alert via the user interface 16 indicating as such, and/or perform other safety functions such as disabling firing stroke activation.

In some examples, the end effector drive system 60 can be used to control an energy sealing instrument. In such examples, the treatment modality can include utilizing the energy sealing instrument for tissue sealing and/or dissection. The motor control circuit 71 can be configured to determine a tissue property (e.g., thickness and/or tissue tension) based at least in part on the mathematical feature (e.g., initial force/torque $F\_0$ or decay time constant $\alpha$ of FIGS. 7A and 7B). The motor control circuit 71 can be configured to identify an energy sealing instrument accessory, determine an applied energy magnitude, and/or determine applied energy duration based at least in part on the tissue property. The energy sealing instrument may be configured to work with an energy sealing accessory that is configured to heat tissue through resistive heating and/or frictional heating.

The end effector drive system 60, in its various alternative configurations, can be configured with a robotic surgical stapling system 15 (FIG. 1) and/or a handheld powered surgical stapler 10 (FIG. 2). Specifically, the end effector 40, motor assembly 78, and motor control circuit 71 can be configured with a robotic surgical stapling system 15 and/or a handheld powered surgical stapler 10.

FIG. 10 is a flow diagram illustrating steps of a method 90 for determining a treatment modality during a clamping time period and providing user feedback. Aspects of the method 90 can be realized as software controlling the end effector drive system (FIG. 6), robotic surgical stapling system 15 (FIG. 1), handheld powered surgical stapler 10 (FIG. 2), variations thereof and alternatives thereto as understood by a person skilled in the pertinent art.

At block 91, motor torque/clamping force is monitored when driving jaws of an end effector which are clamped on tissue with relaxation. For instance, the motor torque/clamping force can be monitored by a motor control circuit configured similarly to the motor control circuit 71 illustrated in FIG. 6, variation thereof, or alternative thereto as understood by a person skilled in the pertinent art. Motor torque and/or clamping force may be measured directly (e.g., by force and/or torque sensors) or indirectly (e.g., calculated based on motor speed and power) as understood by a person skilled in the pertinent art. In some examples, the motor torque/clamping force may follow a profile similar to as illustrated in FIGS. 7A and 7B.

At block 92, the initial relaxation clamping force/torque is identified and recorded. For instance, the start force/torque $F\_0$ at a start time t_start of a tissue relaxation time period t_relaxation (FIGS. 7A and 7B) can be identified and recorded.

At block 93, a tissue thickness can be predicted using a pre-learned model. For instance, tissue thickness can be equal to a function of a maximum force or torque (F_max) at the start of a tissue relaxation time period, indicated as F_0 in FIGS. 7A and 7B. In some examples, the tissue thickness can be linearly related (e.g., approximately linearly correlated, or linearly correlated over a majority of a range of thicknesses) to F_0/F_max.

At block 94, a computer logic can suggest a reload type/color based on predicted tissue thickness. For instance, the surgical instrument utilizing the method 90 can function with a reload type stapling accessory that is type and/or color coded based on an indicated tissue thickness, and software controlling the motor control circuit of the surgical instrument can be configured to suggest at least one reload type/color that is indicated for use on tissue having thickness consistent with the thickness of the tissue predicted at block 93.

At block 95, information related to the installed reload type can be input into the surgical instrument. For instance, the reload may include an electronic identifier that can automatically recognized by the motor control circuit when the reload is installed in the surgical instrument. Additionally, or alternatively, a user such as a surgeon or physician, can input reload information into the user interface of the surgical instrument. Regardless as to how the reload information is entered, the motor control circuit can be configured to receive information regarding the reload and associate the reload with an indicated tissue thickness (e.g., range of tissue thicknesses to be used for).

At block 96, the installed reload type can be compared to one or more suggested reload types. For instance, the one or more reload type/color suggested at block 94 can be compared to the information related to the installed reload type input at block 95. If the installed reload type matches one of the suggested reloads, the method 90 can proceed to block 97. If not, the method 90 can proceed to block 98.

At block 97, no reload change is necessary, and the method 90 can proceed to the next stage of treatment.

At block 98, the installed reload type does not match one of the suggested reloads, and if the tissue is thick and requires an upsize in reload compared to the installed reload, the method 90 can proceed to block 99. If the tissue does not require an upsize in the reload, the method 90 can proceed to block 97, where no reload change is necessary. The determination as to whether the tissue is thick and requires the reload to be upsized can be based on the comparison of the installed reload to the suggested reload types at block 96 and/or predicted tissue thickness determined at block 93.

At block 99, a message can be displayed to the user (e.g., surgeon) to indicate that a reload upsize is appropriate given the thickness of the clamped tissue. For instance, the motor control circuit can be configured to cause a display on the user interface of the surgical instrument or system to display "tissue is too thick, upsize reload", or similar message.

While the method 90 illustrates one example directed toward a surgical stapler that utilizes a cartridge reload, the method can be modified to evaluate and suggest other types of surgical stapler accessories such as replaceable end effectors. Further, the method 90 can be modified to address tissue-thickness dependent treatment modalities related to energy sealing by resistive heating and/or frictional heating such as identifying an energy sealing instrument accessory, determining an applied energy magnitude for energy sealing, and/or determining applied energy duration for energy sealing based on tissue thickness predicted at block 93.

Figure 11:
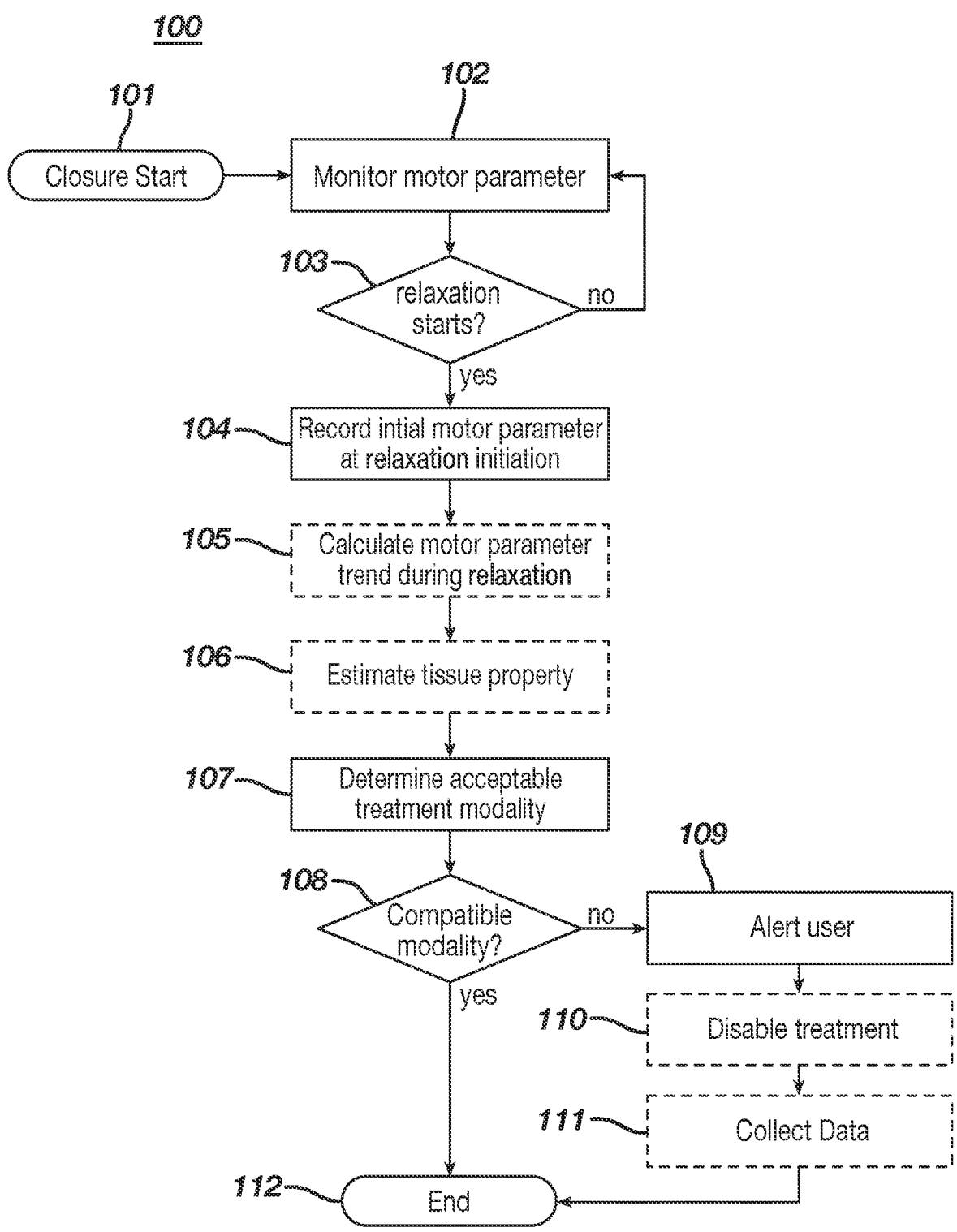
FIG. 11 is a flow diagram illustrating another method for determining a treatment modality during a relaxation time period and providing user feedback.

FIG. 11 is a flow diagram illustrating steps of another method 100 for determining a treatment modality during a clamping time period and providing user feedback. Aspects of the method 100 can be realized as software controlling the end effector drive system (FIG. 6), robotic surgical stapling system 15 (FIG. 1), handheld powered surgical stapler 10 (FIG. 2), variations thereof and alternatives thereto as understood by a person skilled in the pertinent art.

At block 101 closure of the surgical instrument onto tissue begins. For instance, jaws 41, 42 of an end effector 40 can rotate toward each other to close on tissue TT such as illustrated in FIG. 3, 4A, and 4B.

At block 102, a motor parameter can be monitored. For instance, motor torque, force, and/or speed can be monitored during a closure time period (t_close, FIGS. 7A and 7B).

At block 103, the method 100 can determine whether a tissue has begun to relax during a clamping time period. For instance, the motor parameter can be evaluated, and a change in the characteristic of the motor parameter can indicate that a closure time period has ended, and a tissue relaxation time period has begun. Additionally, or alternatively, the start of the tissue relaxation time period can be determined when jaws of the surgical instrument can reach a predetermined position (e.g., predetermined angle or distance of separation). Additionally, or alternatively, the start of the tissue relaxation time period can be determined when the motor shaft has rotated through a predetermined number of rotations.

At block 104, an initial motor parameter can be recorded at initiation of tissue relaxation. For instance, motor torque, force, or speed can be recorded at tissue relaxation initiation. In some examples, motor torque/force can have a profile similar to as illustrated in FIG. 7A and 7B, and the method 100 can be configured to extract the maximum, initial motor torque/force F_0 at the beginning t_start of the tissue relaxation time period t_relaxation. The beginning of the tissue relaxation time period t_start can include a singular point in time or a short duration of time.

At optional block 105, a motor parameter trend can be calculated during the tissue relaxation time period. For instance, the motor parameter may follow a mathematical trend through at least a portion of the tissue relaxation time period that can be characterized by a parameter. As illustrated in FIG. 7B, the motor torque/force decays exponentially with a time constant $\alpha$.

At optional block 106, a tissue property can be estimated. For instance, tissue thickness and/or viscosity can be a function of the initial motor parameter recorded at block 104, and the tissue thickness, tension, and/or viscosity can be estimated based at least in part on the initial motor parameter. FIG. 8 illustrates an example in which tissue thickness is linearly related to initial motor torque/force F_0. Tissue thickness can be estimated based on this correlation or other such mathematical correlation as understood by a person skilled in the pertinent art. Optionally, the tissue property can also be estimated based on the motor parameter trend calculated at block 105. In some examples, tissue thickness is determined based on expected thickness after some amount of compression, for instance compression for approximately 15 seconds with an applied pressure of approximately 9 g/mm$^2$.

At block 107, an acceptable treatment modality can be determined. The treatment modality can be determined based at least in part on the initial motor parameter recorded at block 104. For instance, a surgical stapler accessory or an energy tool treatment modality can be determined based at least in part on the initial motor parameter recorded at block 104. In examples including optional block 106, the treatment modality can be determined based on the estimated tissue property. For instance, an initial motor torque/force can be recorded at block 104 as illustrated in FIGS. 7A and 7B, this initial motor torque/force can be used to determine a tissue thickness at block 106 according to a correlation as illustrated in FIG. 8, and that tissue thickness can be used to select a treatment modality that has an indicated tissue thickness such as selection of one or more of the cartridge types illustrated in FIGS. 9A and 9B. Note that, calculating tissue thickness at block 106 is an intermediate step to arrive at determination of an acceptable treatment modality at block 107; however, the inventors contemplate that a treatment modality may be calculated directly from the initial motor parameter recorded at block 104 without necessarily requiring that the tissue property is explicitly characterized.

At block 108, the method 100 determines whether or not the surgical instrument is configured with a compatible treatment modality. For instance, the surgical instrument may have a stapling accessory such as a cartridge reload or an end effector installed that is indicated for use with a predetermined tissue thickness, and the method 100 may determine whether or not the installed stapling accessory is compatible with the clamped tissue. For an energy tool, the method 100 may determine whether an energy accessory or a power delivery configuration is compatible with the clamped tissue. The determination may be based on a comparison of the treatment modality configuration of the surgical instrument to one or more acceptable treatment modalities determined at block 107. If the surgical instrument is configured with an incompatible treatment modality, the method 100 can proceed to block 109, otherwise the method can proceed to end block 112.

At block 109, a user alert can be provided. The user alert can provide an indication that the surgical instrument is configured with treatment modality that is incompatible with the clamped tissue. For instance, a visual indication or an audible alert can be provided via a user interface of the surgical instrument or system. The alert can indicate that a stapling accessory such as a cartridge reload or end effector is incompatible with tissue. For energy tools, the alert can indicate that an energy sealing instrument accessory, configured energy magnitude, and/or configured energy duration is incompatible with the clamped tissue. Additionally, or alternatively, the alert can provide an indication of an undesirable tissue property. The alert and other tissue information can be provided at the user interface in real time.

At optional block 110, a treatment can be disabled. For instance, a stapling firing stroke, transection, and/or energy delivery, can be disabled in response to a determination at block 108 that the surgical instrument is configured with a treatment modality that is incompatible with the clamped tissue.

At optional block 111 data related to the motor parameter recorded at block 104, motor parameter trend calculated at block 105, tissue property estimated at block 106, treatment modality determined at block 107, and user's reaction to the alert at block 109 (e.g., subsequent treatment modality selection and procedure parameters), other data related to the method 100, or any sub-combination thereof can be collected at block 111 for use in future surgical instrument design and software configuration. For instance, the estimated tissue thickness from real-world surgical procedures can be collected by the computer system of robotic/handheld surgical tools to form a dataset that could be leveraged for next-generation smart instrument designs.

At block 112, the method 100 can end and the surgical instrument can proceed to be operated in subsequent treatment steps such as deploying surgical staples, performing transection, and/or delivering sealing energy.

FIG. 12A is a flow diagram illustrating steps of another method 150 for determining a treatment modality during a clamping time period. Aspects of the method 150 can be realized as software controlling the end effector drive system (FIG. 6), robotic surgical stapling system 15 (FIG. 1), handheld powered surgical stapler 10 (FIG. 2), variations thereof and alternatives thereto as understood by a person skilled in the pertinent art.

At block 152, a motor of a surgical instrument can be electrically driven during a clamping time period including a tissue relaxation time period such that tissue relaxes between a pair of jaws of an end effector of the surgical instrument during the tissue relaxation time period as a result of being driven by the motor.

At block 154, a motor parameter of the motor can be monitored during at least a portion of the tissue relaxation time period.

At block 156, a mathematical feature of the motor parameter during at least the portion of the tissue relaxation time period can be extracted.

At optional block 158, the mathematical feature can be compared to a linear correlation to tissue thickness.

At optional block 160, a tissue property can be estimated based at least in part on the mathematical feature.

At optional block 162, a tissue profile map including the tissue property can be built based at least in part on data from multiple mapping events.

At block 164, a treatment modality can be determined based at least in part on the mathematical feature.

Figure 12B:
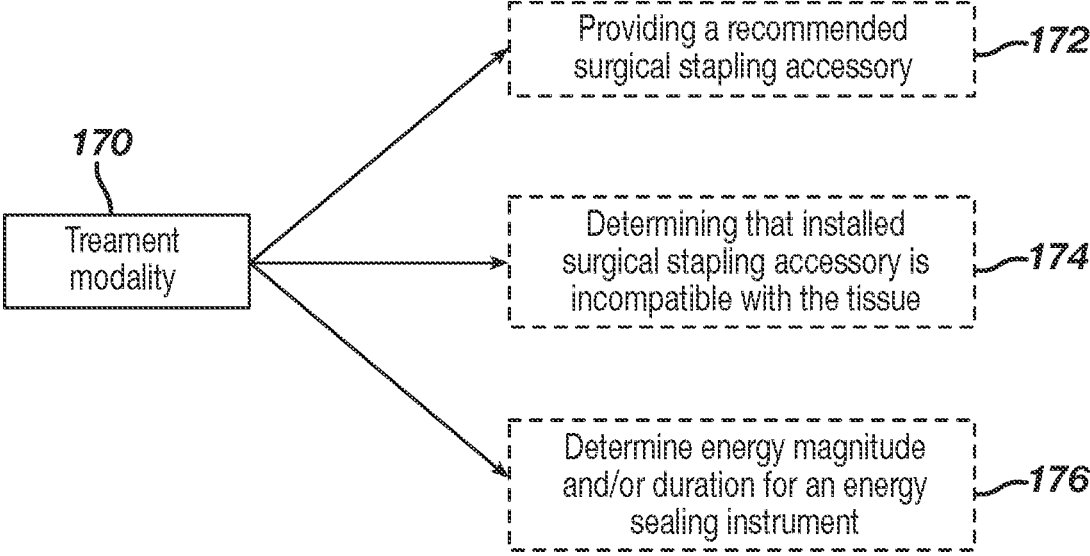
FIG. 12B is block diagram illustrating optional aspects of the method 150 illustrated in FIG. 12A.

FIG. 12B is block diagram illustrating optional aspects of method 150 as it relates to various treatment modalities 170.

At block 172, the method 150 can include providing a recommended surgical stapling accessory.

At block 174, the method 150 can include determining that an installed surgical stapling accessory is incompatible with clamped tissue.

At block 176, the method 150 can determine energy magnitude and/or duration for an energy sealing instrument.

FIG. 13 is an illustration of a sectional view of the end effector 40 illustrated in FIGS. 1 and 2. The end effector 40 is at an open position with the knife 43 at a home position X0 prior to initiating clamping. A firing bar 31 extends in the proximal direction PD into the shaft 30. The firing bar 31 is translatable in the distal direction DD and the proximal direction PD. The knife 43 is positioned on a distal end of the firing bar 31. An I-beam 45 is coupled to the knife 43 and the distal portion of the firing bar 31. The firing bar pushes the I-beam 45 which has extensions that travel through an I-beam channel 55 of the anvil 41 and through an I-beam channel (not illustrated) of the staple jaw 42 to cause the anvil 41 to rotate toward the staple jaw 42 during the relaxation time period and to maintain closure of the jaws 41, 42 during a firing stroke. During the clamping time period, the I-beam 45 engages a shoulder 56 at a proximal end of the I-beam channel 55 through the anvil 41 to cause the anvil 41 to rotate toward the staple jaw 42.

The illustrated clamping assembly includes the firing bar 31 and I-beam 45. The firing bar 31 and I-beam 45, together with the knife 43, and a wedge sled 52 constitute a firing assembly that can be driven by a motor assembly (e.g., motor assembly 78 in FIG. 6) during the firing stroke to deploy staples 51. The illustrated end effector 40 therefore has a clamping/firing assembly.

FIGS. 14A through 14D are a sequence of illustrations of a clamping assembly of an end effector during a closing time period t_close and a tissue relaxation time period t_relaxation. The clamping assembly illustrated in FIGS. 14A through 14D operates similarly to the clamping assembly illustrated in FIG. 13. The firing bar 31, knife 43, and wedge sled 52 are not illustrated for the sake of simplicity. Similar to as illustrated in FIG. 13, the I-beam 45 includes extensions that engage an I-beam channel in the staple jaw 42 and an I-beam channel 55 in the anvil 41. The I-beam channel 55 in the anvil 41 has a shoulder 56.

FIG. 14A shows the anvil 41 in an open position similar to as illustrated in FIG. 13.

FIG. 14B shows the I-beam 45 engaging the shoulder 56 of the I-beam channel 55 of the anvil 41. The I-beam 45 may experience transient forces upon engagement of the shoulder 56. The motor control circuit 71 need not record data related to knife force, tissue compression force, motor torque, or alternative motor parameter until after the transients have subsided.

FIG. 14C shows that the anvil 41 has closed to a small enough angle Θ so that tissue is engaged. FIG. 14C represents the beginning t_start of the relaxation time period t_relaxation. In some examples, the relaxation time period t_relaxation begins when the anvil 41 is closed to a predetermined angle Θ.

FIG. 14D shows that as the I-beam 45 continues to travel distally during the relaxation time period, the angle Θ between the anvil 41 and the staple jaw 42 continues to reduce. Accordingly, the tissue between the anvil 41 and staple jaw 42 is compressed and reduces in thickness. As the I-beam 45 traverses distally from the position illustrated in FIG. 14C to the position illustrated in FIG. 14D, the force on the tissue decays exponentially, and motor torque decays exponentially.

At the conclusion of the clamping time period, the I-beam 45 can continue to travel distally through a firing stroke, preferably at a significantly faster speed.

The end effectors 40 illustrated in FIGS. 13 and 14A through 14D can be operated using the systems and methods described elsewhere herein to determine treatment modality during clamping and other related functions.

The following clauses list non-limiting embodiments of the disclosure:

Clause 1. A surgical instrument (10, 11) comprising: an end effector (40) comprising a pair of jaws (41, 42); a motor assembly (78) comprising a motor (63) mechanically coupled to the end effector (40), the motor assembly (78) being configured to actuate the end effector (40) to grasp and compress tissue (TT) between the pair of jaws (41, 42); and a motor control circuit (71) configured to: electrically drive the motor (63) during a tissue relaxation time period (t_relaxation) during which tissue relaxes between the pair of jaws, monitor a motor parameter of the motor (63) during at least a portion of the tissue relaxation time period (t_relaxation), extract a mathematical feature (F_0, α) of the motor parameter during at least a portion of the clamping time period (t_clamp), and determine a treatment modality based at least in part on the mathematical feature (F_0, α).

Clause 2. The surgical instrument (10, 11) of clause 1, wherein the motor control circuit (71) is configured to extract the mathematical feature (F_0, α) of the motor parameter at a start time (t_start) of the tissue relaxation time period (t_relaxation).

Clause 3. The surgical instrument (10, 11) of clause 2, further comprising: a firing driver configured to translate distally, thereby causes closure of the pair of jaws (41, 42) during a preceding closing time period (t_close) which precedes the tissue relaxation time period (t_relaxation), and wherein the start time (t_start) of the tissue relaxation time period (t_relaxation) occurs when the pair of jaws (41, 42) are closed to a predetermined angle (Θ).

Clause 4. The surgical instrument (10, 11) of clause 2 or 3, wherein the start time (t_start) is determined based at least in part on an exponential curve fit to an initial portion of the tissue relaxation time period (t_relaxation).

Clause 5. The surgical instrument (10, 11) of any one of clauses 1-4, wherein the motor parameter comprises a speed, torque and/or force of the motor.

Clause 6. The surgical instrument (10, 11) of clause 5, wherein the mathematical feature (F_0, α) comprises a value of the speed, torque and/or force (F_0) at a singular predetermined time (t_start) during the tissue relaxation time period (t_relaxation).

Clause 7. The surgical instrument (10, 11) of any one of clauses 1-6, wherein the motor control circuit (71) is configured to: extract a time constant (α) of an exponential decay model of the motor parameter during the tissue relaxation time period (t_relaxation) such that the mathematical feature (F_0, α) comprises the time constant (α) and/or such that the time constant (α) is supplemental to the mathematical feature (F_0, α); and determine the treatment modality based at least in part on the time constant (α).

Clause 8. The surgical instrument (10, 11) of any one of clauses 1-7, wherein the motor control circuit (71) is configured to compare the mathematical feature (F_0, α) to a linear correlation to tissue thickness.

Clause 9. The surgical instrument (10, 11) of clause 8, wherein tissue thickness is determined based at least in part on an expected thickness after compression (d_final).

Clause 10. The surgical instrument (10, 11) of clause 9, wherein the tissue thickness is based at least in part on the expected thickness (d_final) after approximately 15 seconds of compression of the tissue with an applied pressure of approximately 8 g/mm².

Clause 11. The surgical instrument (10, 11) of any one of clauses 1-10, wherein the control circuit is configured to determine, based at least in part on the mathematical feature (F_0, α), a tissue property comprising a thickness and/or tissue tension.

Clause 12. The surgical instrument (10, 11) of clause 11, wherein the motor control circuit (71) is configured to: determine that the tissue property is undesirable, and provide a user indication representing the undesirable tissue property.

Clause 13. The surgical instrument (10, 11) of clause 11 or 12, wherein the motor control ci1rcuit (71) is configured to provide the determination of the tissue property in real time to a user interface (16).

Clause 14. The surgical instrument (10, 11) of any one of clauses 11-13, wherein the motor control circuit (71) is configured to retain data related to the tissue property from multiple clamping events during a surgical procedure.

Clause 15. The surgical instrument (10, 11) of clause 14, wherein the motor control circuit (71) is configured to build a tissue profile map based at least in part on the retained data from multiple clamping events.

Clause 16. The surgical instrument (10, 11) of any one of clauses 1-15, wherein the treatment modality comprises utilization of a surgical stapling accessory (40, 50) indicated for use on a predetermined tissue thickness, and wherein the motor control circuit (71) is configured to identify the predetermined tissue thickness for selection of the surgical stapling accessory (40, 50).

Clause 17. The surgical instrument (10, 11) of clause 16, wherein the motor control circuit (71) is configured to compare the mathematical feature (F_0, α) to a correlation model based on data collected from use of a plurality of surgical stapling accessories (40, 50) indicated for use on disparate predetermined tissue thickness.

Clause 18. The surgical instrument (10, 11) of clause 16, wherein the motor control circuit (71) is configured to compare the mathematical feature (F_0, α) to a correlation model based on data collected from use of a plurality of surgical stapling accessories (40, 50) indicated for use on a predetermined thickness consistent with a predetermined thickness indication for an installed surgical stapling accessory (40, 50) of the surgical instrument (10, 11).

Clause 19. The surgical instrument (10, 11) of any one of clauses 16-18, wherein the surgical stapling accessory (40, 50) comprises a cartridge reload (50).

Clause 20. The surgical instrument (10, 11) of any one of clauses 16-18, wherein the surgical stapling accessory (40, 50) comprises a replaceable end effector (40).

Clause 21. The surgical instrument (10, 11) of any one of clauses 16-20, further comprising a user interface (16), wherein the motor control circuit (71) is configured to provide a recommendation for the surgical stapling accessory (40, 50) via the user interface (16), based at least in part on the selection of the surgical stapling accessory (40, 50).

Clause 22. The surgical instrument (10, 11) of any one of clauses 16-21, wherein the control circuit is configured to: receive data indicating the predetermined thickness indicated for an installed surgical stapling accessory (40, 50), and determine that the installed surgical stapling accessory (40, 50) is incompatible with tissue grasped by the pair of jaws (41, 42) of the end effector (40).

Clause 23. The surgical instrument (10, 11) of clause 22, further comprising a user interface (16), wherein the motor control circuit (71) is configured to provide a user alert to the user interface (16) indicating that the installed surgical stapling accessory (40, 50) is incompatible with tissue grasped by the pair of jaws (41, 42) of the end effector (40).

Clause 24. The surgical instrument (10, 11) of clause 22 or 23, wherein the motor control circuit (71) is configured to disable a firing stroke activation in response to determining that the installed surgical stapling accessory (40, 50) is incompatible with tissue grasped by the pair of jaws (41, 42) of the end effector (40).

Clause 25. The surgical instrument of any one of clauses 1-24, wherein the treatment modality comprises utilization of an energy sealing instrument, and wherein the motor control circuit (71) is configured to: determine, based at least in part on the mathematical feature (F_0, α), a tissue property comprising a thickness and/or tissue tension, and identify an energy sealing instrument accessory, determine an applied energy magnitude, and/or determine applied energy duration based at least in part on the tissue property.

Clause 26. The surgical instrument of clause 25, wherein the treatment modality further comprises tissue dissection.

Clause 27. The surgical instrument of clause 25 or 26, wherein the energy sealing accessory is configured to heat tissue through resistive heating and/or frictional heating.

Clause 28. The surgical instrument (11) of any one of clauses 1-27, wherein the end effector (40), motor assembly (78), and motor control circuit (71) are configured with a robotic surgical stapling system (15).

Clause 29. The surgical instrument (10) of any one of clauses 1-27, wherein the end effector (40), motor assembly (78), and motor control circuit (71) are configured with a handheld powered surgical stapler (10).

Clause 30. A method comprising: electrically driving a motor (63) of a surgical instrument (10, 11) during a tissue relaxation time period (t_relaxation), such that tissue relaxes between jaws of a pair of jaws (41, 42) of an end effector (40) of the surgical instrument (10, 11) during the tissue relaxation time period (t_relaxation) as a result of being driven by the motor; monitoring a motor parameter of the motor (63) during at least a portion of the tissue relaxation time period (t_relaxation); extracting a mathematical feature (F_0, α) of the motor parameter during at least the portion of the tissue relaxation time period (t_relaxation); and determining a treatment modality based at least in part on the mathematical feature (F_0, α).

Clause 31. The method of clause 30, further comprising: extracting the mathematical feature (F_0, α) of the motor parameter at a start time (t_start) of the tissue relaxation time period (t_relaxation).

Clause 32. The method of clause 31, comprising: electrically driving a motor (63) of a surgical instrument (10, 11), during a closure time period (t_close) prior to the tissue relaxation time period (t_relaxation) in which an angle (Θ) between the jaws of the pair of jaws (41, 42) is reduced, wherein the start time (t_start) of the tissue relaxation time period (t_relaxation) occurs when the jaws (41, 42) are closed to a predetermined angle (Θ).

Clause 33. The method of clause 31 or 32, wherein the start time (t_start) is determined based at least in part on an exponential curve fit to an initial portion of the tissue relaxation time period (t_relaxation).

Clause 34. The method of any one of clauses 30-33, wherein the motor parameter comprises a speed, torque and/or force of the motor.

Clause 35. The method of clause 34, wherein the mathematical feature (F_0, α) comprises a value of the speed, torque and/or force (F_0) at a singular predetermined time (t_start) during the tissue relaxation time period (t_relaxation).

Clause 36. The method of clause 30, comprising: extracting a time constant of an exponential decay model of the motor parameter during the tissue relaxation time period (t_relaxation) such that the mathematical feature (F_0, α) comprises the time constant and/or such that the time constant is supplemental to the mathematical feature (F_0, α); and determining the treatment modality based at least in part on the time constant.

Clause 37. The method of any one of clauses 30-36, comprising: comparing the mathematical feature (F_0, α) to a linear correlation to tissue thickness.

Clause 38. The method of clause 37, wherein tissue thickness is determined based at least in part on an expected thickness after compression (d_final).

Clause 39. The method of clause 38, wherein the tissue thickness is based at least in part on the expected thickness (d_final) after approximately 15 seconds of compression of the tissue with an applied pressure of approximately 8 g/mm².

Clause 40. The method of any one of clauses 30-39, determining, based at least in part on the mathematical feature (F_0, α), a tissue property comprising a thickness and/or tissue tension.

Clause 41. The method of clause 40, comprising: determining that the tissue property is undesirable, and providing a user indication representing the undesirable tissue property.

Clause 42. The method of clause 40 or 42, comprising: providing the tissue property to a user interface (g) in real time.

Clause 43. The method of any one of clauses 40-42, comprising: retaining data related to the tissue property from multiple clamping events during a surgical procedure.

Clause 44. The method of clause 43, comprising: building a tissue profile map based at least in part on the retained data from multiple clamping events.

Clause 45. The method of any one of clauses 30-44, comprising: identifying surgical stapling accessory (40, 50) indicated for use on a predetermined tissue thickness based at least in part on the mathematical feature (F_0, α), wherein the treatment modality comprises utilization of the surgical stapling accessory (40, 50).

Clause 46. The method of clause 45, comprising: comparing the mathematical feature (F_0, α) to a correlation model based on data collected from use of a plurality of surgical stapling accessories indicated for use on disparate predetermined tissue thickness.

Clause 47. The method of clause 45 or 46, comprising: comparing the mathematical feature (F_0, α) to a correlation model based on data collected from use of a plurality of surgical stapling accessories indicated for use on a predetermined thickness consistent with a predetermined thickness indication for an installed surgical stapling accessory (40, 50) of the surgical instrument (10, 11).

Clause 48. The method of any one of clauses 45-47, wherein the surgical stapling accessory (40, 50) comprises a cartridge reload (50).

Clause 49. The method of any one of clauses 45-47, wherein the surgical stapling accessory (40, 50) comprises a replaceable end effector (40).

Clause 50. The method of any one of clauses 45-49, comprising: providing a recommendation for the surgical stapling accessory (40, 50), at a user interface (16), based at least in part on the selection of the surgical stapling accessory (40, 50).

Clause 51. The method of any one of clauses 45-50, comprising: receiving data indicating the predetermined thickness indicated for an installed surgical stapling accessory (40, 50); and determining, that installed surgical stapling accessory (40, 50) is incompatible with the tissue.

Clause 52. The method of clause 51, comprising: providing a user alert to the user interface (16) indicating that the installed surgical stapling accessory (40, 50) is incompatible with tissue grasped by jaws (41, 42) of the end effector (40).

Clause 53. The method of clause 51 or 52, comprising: disabling a firing stroke activation in response to determining that the installed surgical stapling accessory (40, 50) is incompatible with tissue grasped by jaws (41, 42) of the end effector (40).

Clause 54. The method of any one of clauses 30-53, comprising: determining, based at least in part on the mathematical feature (F_0, α), a tissue property comprising a thickness and/or tissue tension; and identify an energy sealing instrument accessory based at least in part on the tissue property.

Clause 55. The method of clause 54, comprising: determining, based at least in part on the mathematical feature (F_0, α), a tissue property comprising a thickness and/or tissue tension; and determining an applied energy magnitude and/or applied energy duration of the energy sealing instrument based at least in part on the tissue property.

Clause 56. The method of clauses 54 or 55, further comprising: heating tissue through resistive heating and/or frictional heating.

Having shown and described exemplary embodiments of the subject matter contained herein, further adaptations of the methods and systems described herein may be accomplished by appropriate modifications without departing from the scope of the claims. For instance, software methods can be realized in various types of hardware; and software methods can include additional steps; surgical instruments, tools, and system illustrated and described herein can be modified to include alternative and/or additional compatible features of other surgical instruments, tools, and systems known in the art or yet to be developed. In addition, where methods and steps described above indicate certain events occurring in certain order, it is intended that certain steps do not have to be performed in the order described, but in any order, as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

What is claimed is:

1. A surgical instrument comprising:
an end effector comprising a pair of jaws;
a motor assembly comprising a motor mechanically coupled to the end effector, the motor assembly being configured to actuate the end effector to grasp and compress tissue between the pair of jaws; and
a motor control circuit configured to:
electrically drive the motor during a tissue relaxation time period during which tissue relaxes between the pair of jaws,
monitor a motor parameter of the motor during at least a portion of the tissue relaxation time period,
extract a mathematical feature of the motor parameter at a start time of the tissue relaxation time period, and
determine a treatment modality based at least in part on the mathematical feature.

2. The surgical instrument of claim 1, further comprising:
a firing driver configured to translate distally, thereby causes closure of the pair of jaws during a preceding closing time period which precedes the tissue relaxation time period, and wherein the start time of the tissue relaxation time period occurs when the pair of jaws are closed to a predetermined angle.

3. The surgical instrument of claim 1, wherein the motor parameter comprises a speed, torque and/or force of the motor.

4. The surgical instrument of claim 3, wherein the mathematical feature comprises a value of the speed, torque and/or force at a singular predetermined time during the tissue relaxation time period.

5. The surgical instrument of claim 1, wherein the motor control circuit is configured to:

extract a time constant of an exponential decay model of the motor parameter during the tissue relaxation time period such that the mathematical feature comprises the time constant and/or such that the time constant is supplemental to the mathematical feature; and determine the treatment modality based at least in part on the time constant.

6. The surgical instrument of claim 1, wherein the motor control circuit is configured to compare the mathematical feature to a linear correlation to tissue thickness.

7. The surgical instrument of claim 6, wherein tissue thickness is determined based at least in part on an expected thickness after compression.

8. The surgical instrument of claim 1, wherein the treatment modality comprises utilization of a surgical stapling accessory indicated for use on a predetermined tissue thickness, and wherein the motor control circuit is configured to identify the predetermined tissue thickness for selection of the surgical stapling accessory.

9. The surgical instrument of claim 8, wherein the motor control circuit is configured to compare the mathematical feature to a correlation model based on data collected from use of a plurality of surgical stapling accessories indicated for use on disparate predetermined tissue thickness.

10. The surgical instrument of claim 8, wherein the motor control circuit is configured to compare the mathematical feature to a correlation model based on data collected from use of a plurality of surgical stapling accessories indicated for use on a predetermined thickness consistent with a predetermined thickness indication for an installed surgical stapling accessory of the surgical instrument.

11. The surgical instrument of claim 8, wherein the surgical stapling accessory comprises a cartridge reload.

12. The surgical instrument of claim 8, wherein the surgical stapling accessory comprises a replaceable end effector.

13. The surgical instrument of claim 8, further comprising a user interface, wherein the motor control circuit is configured to provide a recommendation for the surgical stapling accessory, at the user interface, based at least in part on the selection of the surgical stapling accessory.

14. The surgical instrument of claim 8, wherein the motor control circuit is configured to:

receive data indicating the predetermined tissue thickness indicated for an installed surgical stapling accessory, and determine that the installed surgical stapling accessory is incompatible with tissue grasped by the pair of jaws of the end effector.

15. The surgical instrument of claim 14, further comprising a user interface, wherein the motor control circuit is configured to provide a user alert to the user interface indicating that the installed surgical stapling accessory is incompatible with tissue grasped by the pair of jaws of the end effector.

16. The surgical instrument of claim 1, wherein the treatment modality comprises utilization of an energy sealing instrument, and wherein the motor control circuit is configured to:

determine, based at least in part on the mathematical feature, a tissue property comprising a thickness and/or tissue tension, and identify an energy sealing instrument accessory, determine an applied energy magnitude, and/or determine applied energy duration based at least in part on the tissue property.

17. The surgical instrument of claim 1, wherein the start time is determined based at least in part on an exponential curve fit to an initial portion of the tissue relaxation time period.

18. The surgical instrument of claim 1, wherein the motor control circuit is configured to determine, based at least in part on the mathematical feature, a tissue property comprising a thickness and/or tissue tension.

19. The surgical instrument of claim 18, wherein the motor control circuit is configured to retain data related to the tissue property from multiple clamping events during a surgical procedure, and wherein the motor control circuit is configured to build a tissue profile map based at least in part on the retained data from multiple clamping events.

20. A surgical instrument comprising:

an end effector comprising a pair of jaws;

a motor assembly comprising a motor mechanically coupled to the end effector, the motor assembly being configured to actuate the end effector to grasp and compress tissue between the pair of jaws; and a motor control circuit configured to:

electrically drive the motor during a tissue relaxation time period during which tissue relaxes between the pair of jaws, monitor a motor parameter of the motor during at least a portion of the tissue relaxation time period, extract a time constant of an exponential decay model of the motor parameter during the tissue relaxation time period such that a mathematical feature of the motor parameter comprises the time constant and/or such that the time constant is supplemental to the mathematical feature, and determine a treatment modality based at least in part on the time constant.

* * * * *